(12) United States Patent
Shimizu

(10) Patent No.: US 11,773,044 B2
(45) Date of Patent: *Oct. 3, 2023

(54) METHOD FOR PRODUCING ACETIC ACID

(71) Applicant: DAICEL CORPORATION, Osaka (JP)

(72) Inventor: Masahiko Shimizu, Himeji (JP)

(73) Assignee: DAICEL CORPORATION, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/334,667

(22) PCT Filed: May 2, 2018

(86) PCT No.: PCT/JP2018/017508
§ 371 (c)(1),
(2) Date: Mar. 19, 2019

(87) PCT Pub. No.: WO2019/211904
PCT Pub. Date: Nov. 7, 2019

(65) Prior Publication Data
US 2021/0221763 A1  Jul. 22, 2021

(51) Int. Cl.
*C07C 51/12* (2006.01)
*B01J 39/04* (2017.01)
(Continued)

(52) U.S. Cl.
CPC ............. *C07C 51/12* (2013.01); *B01J 39/04* (2013.01); *B01J 47/02* (2013.01); *C07C 51/44* (2013.01); *C07C 51/47* (2013.01)

(58) Field of Classification Search
CPC ......... C07C 53/08; C07C 51/47; C07C 51/12; C07C 51/44; B01J 39/04; B01J 47/02; B01J 31/08
See application file for complete search history.

(56) References Cited

U.S. PATENT DOCUMENTS 4,541,897 A * 9/1985 Sommer ................ B01D 3/146
203/19
5,416,237 A * 5/1995 Aubigne ................. C07C 51/12
562/519
(Continued)

FOREIGN PATENT DOCUMENTS

JP          9-2993 A    1/1997
JP      2014-508820 A   4/2014
(Continued)

OTHER PUBLICATIONS

International Search Report and Written Opinion of the International Searching Authority for International Application No. PCT/JP2018/017508, dated Jun. 26, 2018.
(Continued)

*Primary Examiner* — Yevgeny Valenrod
*Assistant Examiner* — Blaine G Doletski
(74) *Attorney, Agent, or Firm* — Birch, Stewart, Kolasch & Birch, LLP

(57) ABSTRACT

A method for producing acetic acid can improve the life of a silver-substituted ion exchange resin for removing organic iodine compounds in acetic acid. In a carbonylation process of a methanol method, an acetic acid distillation step has at least one distillation step of carrying out the purification of an acetic acid stream under conditions of a column bottom temperature of a distillation column of less than 175° C., a nickel base alloy or zirconium is used as a material of the distillation column in the distillation step, and as metal ion concentrations in a charging mixture of the distillation column in the distillation step, an iron ion concentration is less than 10,000 ppb by mass, a chromium ion concentration is less than 5,000 ppb by mass, a nickel ion concentration is less than 3,000 ppb by mass, and a molybdenum ion concentration is less than 2,000 ppb by mass.

14 Claims, 5 Drawing Sheets

(51) Int. Cl.
   *B01J 47/02*   (2017.01)
   *C07C 51/44*   (2006.01)
   *C07C 51/47*   (2006.01)

(56) References Cited

U.S. PATENT DOCUMENTS

| | | |
|---|---|---|
| 5,696,284 A | 12/1997 | Baker et al. |
| 8,664,283 B2 | 3/2014 | Blanchard et al. |
| 9,409,163 B2 | 8/2016 | Shaver et al. |
| 9,540,304 B2 | 1/2017 | Liu et al. |
| 9,776,944 B2 | 10/2017 | Shimizu et al. |
| 10,457,622 B2* | 10/2019 | Shimizu .................. C07C 51/47 |
| 2012/0202900 A1 | 8/2012 | Blanchard et al. |
| 2013/0264186 A1 | 10/2013 | Shimizu et al. |
| 2014/0128487 A1 | 5/2014 | Shaver et al. |
| 2016/0137576 A1* | 5/2016 | Liu .......................... C07C 51/12 562/519 |
| 2016/0376213 A1* | 12/2016 | Ramage .................. C07C 51/12 562/519 |

FOREIGN PATENT DOCUMENTS

| | | |
|---|---|---|
| JP | 2016-117709 A | 6/2016 |
| WO | WO 2012/086386 A1 | 6/2012 |

OTHER PUBLICATIONS

English translation of International Preliminary Report on Patentability and Written Opinion dated Nov. 12, 2020, in PCT/JP2018/017508 (Forms PCT/IB/338, PCT/IB/373, and PCT/ISA/237).

* cited by examiner

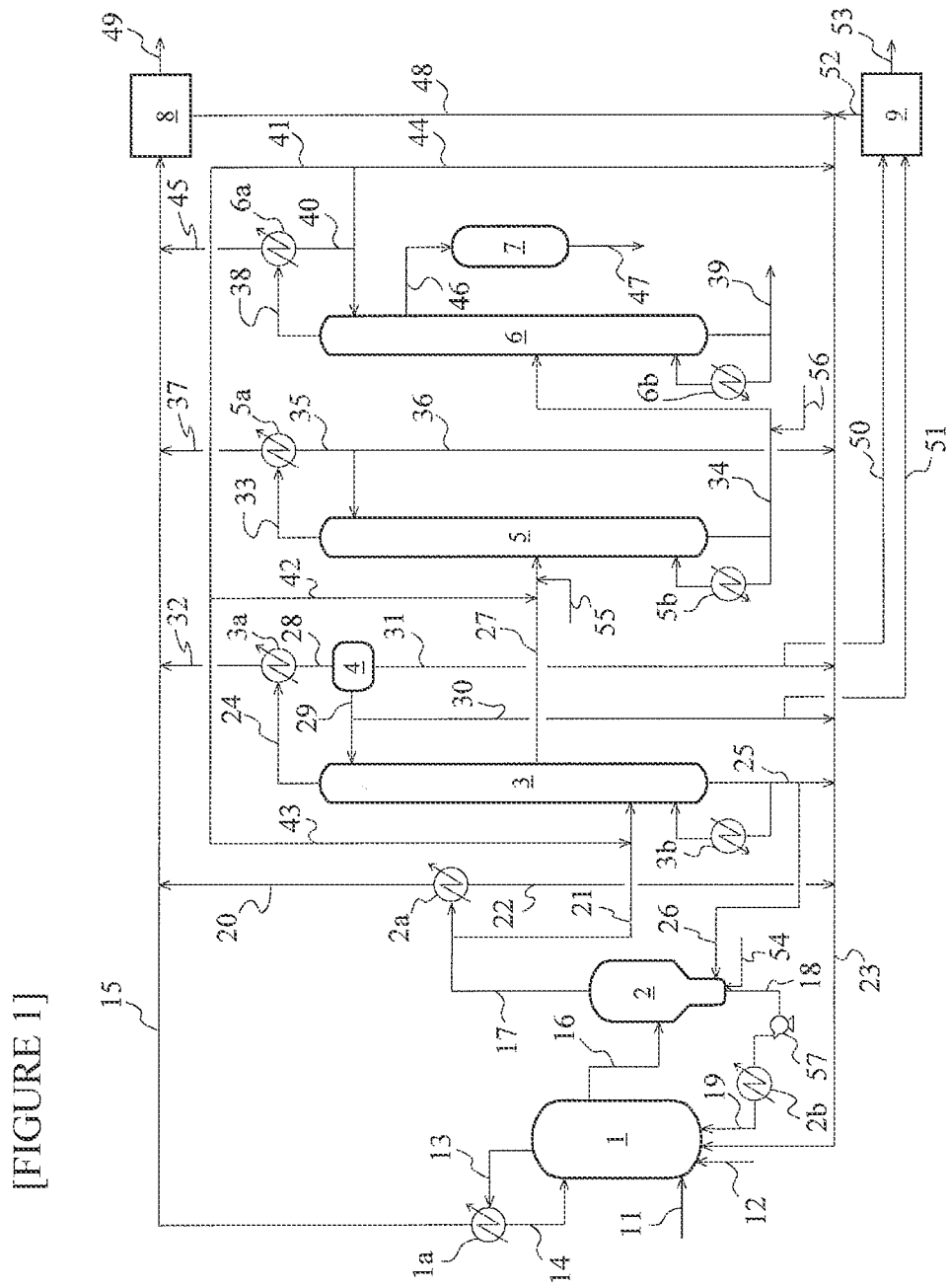
[FIGURE 1]

[FIGURE 2]
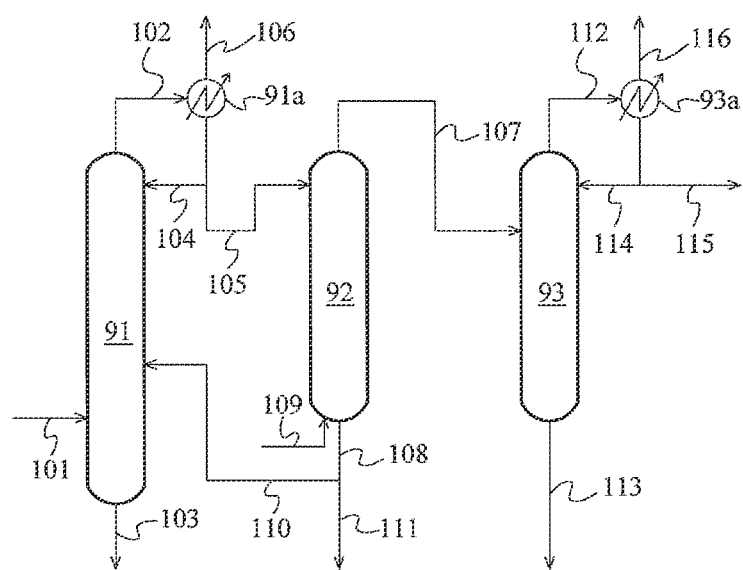

[FIGURE 3]
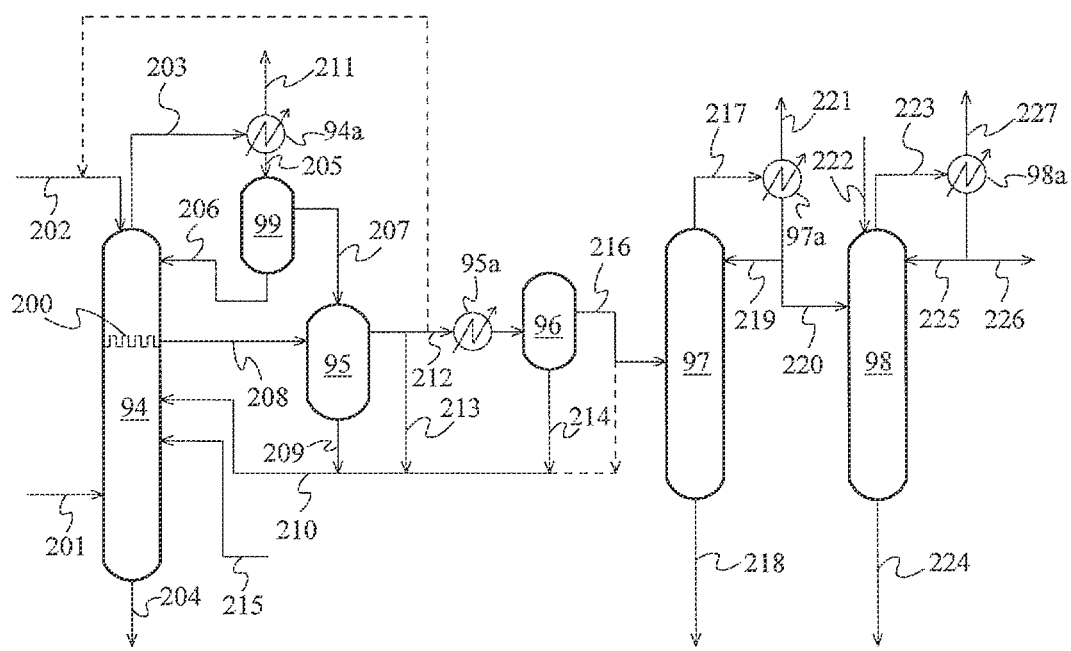

[FIGURE 4]
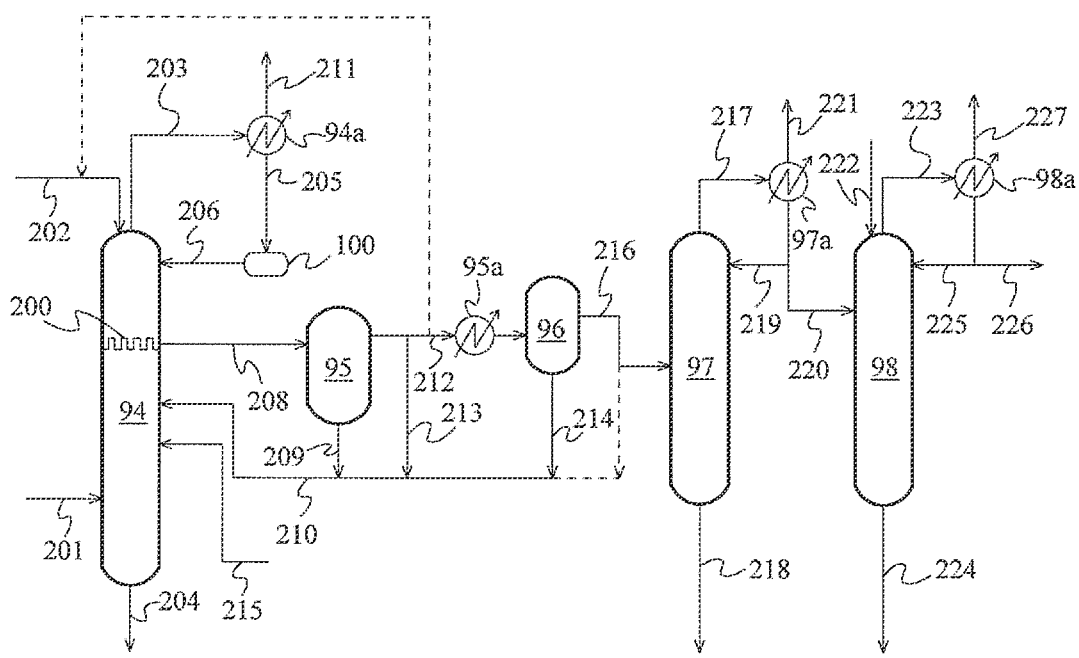

[FIGURE 5]
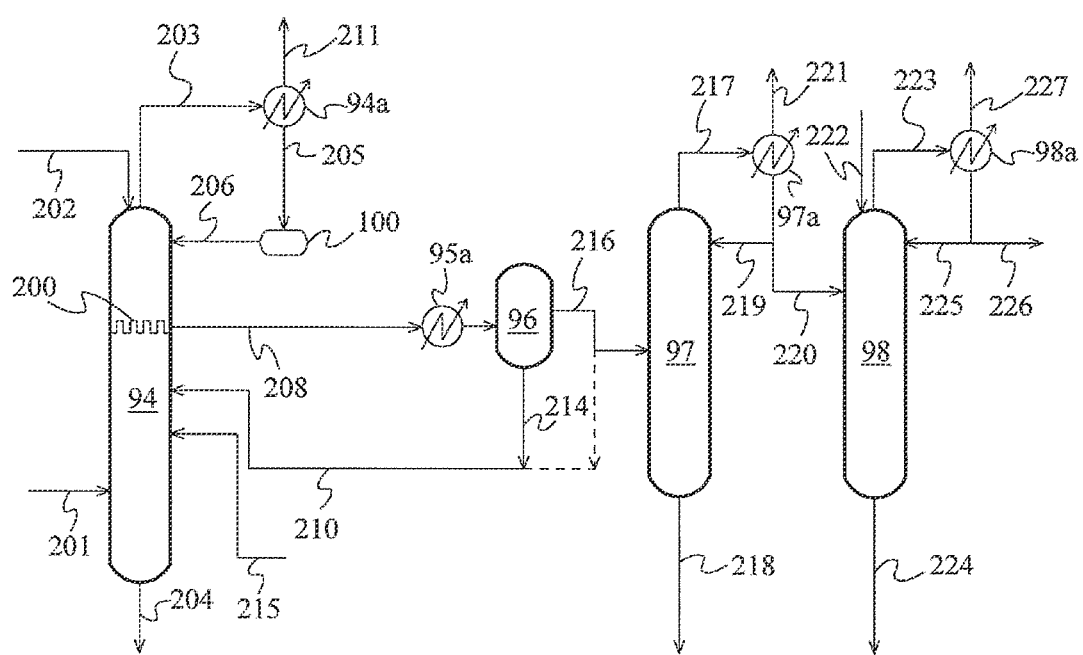

METHOD FOR PRODUCING ACETIC ACID

TECHNICAL FIELD

The present invention relates to a method for producing acetic acid.

BACKGROUND ART

A carbonylation process of a methanol method (an acetic acid process of a methanol method) is known as an industrial method for producing acetic acid. In this process, for example, methanol and carbon monoxide are reacted in the presence of a catalyst in a reaction vessel to produce acetic acid. The reaction mixture is evaporated in an evaporator, and the vapor phase is purified in a lower boiling point component removal column and subsequently in a dehydration column so that product acetic acid is prepared. Alternatively, product acetic acid is prepared via a higher boiling point component removal column subsequent to the dehydration column, and further, a product column.

In such a process for producing acetic acid, organic iodine compounds, such as hexyl iodide, are produced as by-products in the reaction system, and are included as a very small amount of impurities in the product acetic acid. When acetic acid containing organic iodine compounds is used as a raw material for producing vinyl acetate, the palladium catalyst is degraded, and hence there is a need to reduce the organic iodine compound concentration in the acetic acid to an order of a few ppb. Therefore, conventionally, the organic iodine compound concentration in the acetic acid has been reduced to as low as possible by using a cation exchange resin substituted with silver ions. However, in an adsorptive removal method of organic iodine compounds that uses such a silver-substituted ion exchange resin (hereinafter, sometimes referred to as an "IER"), there is a problem that corroded metals (also referred to as "corrosion metals") derived from corrosion in an apparatus, such as iron, nickel, chromium, and molybdenum, and the like present in the process stream undergo ion exchange with the silver in the ion exchange resin, whereby useful silver dissolves into the acetic acid and flows out of the system, causing the organic iodine compound removal life of the ion exchange resin to decrease. Further, as a consequence of that, there is also the problem that the concentration of corrosion metals etc. and the silver concentration in the product acetic acid increase, causing the quality of the product acetic acid to deteriorate.

Patent Literature 1 discloses, a process in which, in order to suppress deterioration in the life of an ion exchange resin due to corroded metals, acetic acid is purified using an ion exchange resin composition including a metal-activated ion exchange resin containing a specific amount of metal-functionalized sites and a non-metal-functionalized ion exchange resin containing non-metal-functionalized sites. Further, Patent Literature 2 discloses a method in which, in order to suppress corrosion of a dehydration column, an alkali component for neutralizing hydrogen iodide, which is a factor in apparatus corrosion, is added and mixed into the dehydration column or the dehydration column feeding solution.

However, none of the above-described methods are capable of sufficiently suppressing deterioration in the life of the ion exchange resin due to corroded metals.

CITATION LIST

Patent Literature

Patent Literature 1: National Publication of International Patent Application No. 2014-508820

Patent Literature 2: International Patent Application No. 2012/086386

SUMMARY OF INVENTION

Technical Problem

Accordingly, an object of the present invention is to provide a method for producing acetic acid capable of greatly improving the life of a silver-substituted ion exchange resin (IER) for removing organic iodine compounds in acetic acid.

Solution to Problem

In order to attain the object, the present inventor has conducted diligent studies focusing on the material of the dehydration column and impurities in the charging mixture of the dehydration column to learn that, by employing a specific material for the material of the dehydration column, and controlling the concentrations of specific metal ions in the dehydration column charging mixture, the metal ion concentrations in the acetic acid obtained from the dehydration column can be maintained at a low level, the metal ion concentrations in the acetic acid fed into the IER in a subsequent adsorptive removal step can be controlled to a low level, thus the life of the IER can be greatly improved, and therefore the deterioration of the quality of the product acetic acid can be prevented.

Further, in order to investigate the causes of the corrosion of the dehydration column, the present inventor first examined the relationship between the composition of the column bottom liquid (also referred to as the bottom fraction) of the distillation column and the column bottom temperature. In the above-mentioned methanol carbonylation process, a metal catalyst such as a rhodium catalyst is used as a catalyst, and methyl iodide is used as a co-catalyst. Therefore, hydrogen iodide is produced as a by-product in the reaction system. Most of the methyl iodide and hydrogen iodide are separated by distillation in the dehydration column, but some hydrogen iodide in the order of ppb or ppm is present in the bottom fraction of the dehydration column. Therefore, an alkali such as potassium hydroxide is charged into the column of the dehydration column or the bottom fraction to neutralize the remaining hydrogen iodide. The produced alkali metal salt (alkali metal iodide or alkali metal acetate) is removed by distillation equipment and the like (e.g., a higher boiling point component removal column) in the next step. Such alkali metal salts are concentrated in the bottom of the distillation column and discarded along with acetic acid from the bottom line, but the waste amount has been kept as low as possible to improve the usage rate of acetic acid. Therefore, the alkali metal salt concentration in the column bottom liquid of the distillation column increases, the boiling point increases due to the salts, and the column bottom temperature (bottom temperature) of the distillation column increases. In addition, the interior of the column is corroded by the hydrogen iodide present in the bottom fraction of the dehydration column and the corroded metal flows out to form metal acetates. Like the alkali metal salts, these metal acetates also have an influence on the increase of the column bottom temperature of the distillation column.

Further, since there is hardly any water at the bottom of the above-mentioned distillation column (e.g., a higher boiling point component removal column), acetic anhydride is produced by a dehydration reaction of acetic acid. When a metal iodide (e.g., iron iodide) produced by corrosion of the distillation equipment by hydrogen iodide is present, this acetic anhydride is produced in a larger amount by a catalytic action of the metal iodide. Therefore, acetic anhydride is abundant in the column bottom liquid of the distillation column, and the column bottom temperature rises.

In addition, higher boiling point impurities such as propionic acid produced as by-products in the reaction system are concentrated at the bottom of the distillation column. These are also a cause of the rise in the column bottom temperature.

Next, based on such investigations and considerations, the present inventor examined, using a corrosion test, the relationship among the kind and amount of higher boiling point impurities present in the column bottom liquid of the distillation column, the column bottom temperature and pressure, and the corrosivity of various materials. As a result, the present inventor confirmed that temperature has a substantial influence on the corrosion rate, and that at temperatures not less than 160° C. only high durability materials such as zirconium or a nickel base alloy such as Hastelloy B2 can be used, that even with pure acetic acid the pressure rises and as the boiling point increases, the corrosion rate increases, that under the same operating pressure, the corrosion rate increases as the concentrations of acetate salts, acetic anhydride, and propionic acid causing an increase in boiling point increase, and that the corrosion rate depends on the type of higher boiling point impurity.

The present invention has been completed based on the above knowledge and through further investigation.

Specifically, the present invention provides a method for producing acetic acid, including:

a carbonylation reaction step of reacting methanol with carbon monoxide in a reaction vessel in the presence of a catalyst system containing a metal catalyst and methyl iodide, acetic acid, methyl acetate, and water to produce acetic acid;

a separation step of using one or more evaporators and/or distillation columns to separate the reaction mixture obtained in the carbonylation reaction step into a stream containing the metal catalyst, an acetic acid stream rich in acetic acid, and a stream more enriched with a lower boiling point component than the acetic acid stream;

an acetic acid distillation step, optionally included in the separation step, of distilling the acetic acid stream to purify the acetic acid; and an adsorptive removal step of treating the purified acetic acid stream obtained in the acetic acid distillation step with an ion exchange resin, wherein the acetic acid distillation step has at least one distillation step of carrying out the purification of the acetic acid stream under conditions of a column bottom temperature of the distillation column of less than 175° C., a nickel base alloy or zirconium is used as a material of the distillation column in the distillation step, and as metal ion concentrations in a charging mixture of the distillation column in the distillation step, an iron ion concentration is less than 10,000 ppb by mass, a chromium ion concentration is less than 5,000 ppb by mass, a nickel ion concentration is less than 3,000 ppb by mass, and a molybdenum ion concentration is less than 2,000 ppb by mass.

It is preferred that the charging mixture of the distillation column in the distillation step have an acetic acid concentration of 90% by mass or more.

It is preferred that the charging mixture of the distillation column in the distillation step contain at least one compound selected from the group consisting of an acetate salt, acetic anhydride, and propionic acid.

It is preferred that a column bottom liquid of the distillation column in the distillation step have an acetate salt concentration of 34% by mass or less.

It is preferred that the column bottom liquid of the distillation column in the distillation step have an acetic anhydride concentration of 90% by mass or less.

It is preferred that the column bottom liquid of the distillation column in the distillation step have a propionic acid concentration of 90% by mass or less.

It is preferred that the distillation be carried out under conditions of a column bottom pressure of the distillation column in the distillation step of less than 0.255 MPaG.

It is preferred that the distillation be carried out under conditions of the column bottom pressure of the distillation column in the distillation step of 0.01 MPaG or more and less than 0.255 MPaG.

It is preferred that a zinc ion concentration in the charging mixture of the distillation column in the distillation step be less than 1,000 ppb by mass.

It is preferred that a plate spacing between a charging mixture feeding plate and a column top vapor withdrawal plate of the distillation column in the distillation step be not less than one plate in terms of actual plates.

It is preferred that the material of a charging pipe to the distillation column in the distillation step be a nickel base alloy or zirconium.

It is preferred that the acetic acid distillation step have at least one distillation step in which the acetic acid concentration in the acetic acid stream to be distilled is 97% by mass or more, and in all such steps the distillation of the acetic acid stream be carried out under conditions of a column bottom temperature of the distillation column of less than 175° C.

The present invention also provides a method for producing acetic acid, including:

a carbonylation reaction step of reacting methanol with carbon monoxide in a reaction vessel in the presence of a catalyst system containing a metal catalyst and methyl iodide, acetic acid, methyl acetate, and water to produce acetic acid;

an evaporation step of separating the reaction mixture obtained in the carbonylation reaction step into a vapor stream and a residual liquid stream in an evaporator;

a lower boiling point component removal step of separating the vapor stream by distillation into an overhead stream rich in a lower boiling point component and a first acetic acid stream rich in acetic acid;

a dehydration step of separating the first acetic acid stream by distillation into an overhead stream rich in water and a second acetic acid stream more enriched with acetic acid than the first acetic acid stream; and an adsorptive removal step of treating the second acetic acid stream, or an acetic acid stream that has been more enriched with acetic acid by further purification of the second acetic acid stream, with an ion exchange resin, wherein a nickel base alloy or zirconium is used as a material of a distillation column in the dehydration step, and as metal ion concentrations in a charging mixture of the distillation column in the dehydration step, an iron ion concentration is less than 10,000 ppb by mass, a chromium ion concentration is less than 5,000 ppb by mass, a nickel ion concentration is less than 3,000 ppb by mass, and a molybdenum ion concentration is less than 2,000 ppb by mass, and the dehydration step is carried out under conditions of a column bottom temperature of the distillation column of less than 175° C.

It is preferred that an iron ion concentration in the second acetic acid stream be less than 21,000 ppb by mass.

It is preferred that as the metal ion concentrations in the second acetic acid stream, the iron ion concentration be less than 21,000 ppb by mass, a chromium ion concentration be less than 7,100 ppb by mass, a nickel ion concentration be less than 4,000 ppb by mass, a molybdenum ion concentration be less than 3,000 ppb by mass, and a zinc ion concentration be less than 1,000 ppb by mass.

The present invention also provides a method for producing acetic acid, comprising, in a distillation column having a nickel base alloy or zirconium as a material and having a plate spacing between a charging mixture feeding plate and a column top vapor withdrawal plate of not less than one plate in terms of actual plates, feeding crude acetic acid having an iron ion concentration of less than 10,000 ppb by mass, a chromium ion concentration of less than 5,000 ppb by mass, a nickel ion concentration of less than 3,000 ppb by mass, a molybdenum ion concentration of less than 2,000 ppb by mass, a zinc ion concentration of less than 1,000 ppb by mass, a hexyl iodide concentration of less than 510 ppb by mass, and an acetic acid concentration of not less than 80% by mass into the charging mixture feeding plate via a charging pipe having a nickel base alloy or zirconium as a material, and conducting distillation under conditions of a column bottom temperature of less than 175° C. to obtain an overhead stream rich in water, and purified acetic acid having an iron ion concentration of less than 21,000 ppb by mass, a chromium ion concentration of less than 7,100 ppb by mass, a nickel ion concentration of less than 4,000 ppb by mass, a molybdenum ion concentration of less than 3,000 ppb by mass, and a zinc ion concentration of less than 1,000 ppb by mass.

Advantageous Effects of Invention

According to the present invention, when purifying acetic acid by distilling a crude acetic acid solution containing acetic acid and an impurity having a boiling point that is higher than that of acetic acid, because the distillation column in the acetic acid distillation step (e.g., dehydration step, higher boiling point component removal step, etc.) is made from a specific material, the distillation is carried out under conditions of a column bottom temperature of the distillation column of less than 175° C., and the concentrations of specific metal ions in the charging mixture to the distillation column are defined to be specific values or less, the metal ion concentrations in the purified acetic acid obtained at the distillation column can be reduced, and as a result the metal ion concentrations in the acetic acid fed to the subsequent adsorptive removal step can also be reduced. As a result, the life of the silver-substituted ion exchange resin (IER) used in the adsorptive removal step can be greatly improved, and the metal ion concentrations in the product acetic acid can also be reduced. The resultant acetic acid having low metal ion concentrations can be utilized as low-metal acetic acid that can be used in electronic material applications.

BRIEF DESCRIPTION OF DRAWINGS

FIG. 1 is an acetic acid production flow diagram showing one embodiment of the present invention.

FIG. 2 is a schematic flow diagram showing one example of an acetaldehyde separation and removal system.

FIG. 3 is a schematic flow diagram showing another example of the acetaldehyde separation and removal system.

FIG. 4 is a schematic flow diagram showing a further alternative example of the acetaldehyde separation and removal system.

FIG. 5 is a schematic flow diagram showing a further alternative example of the acetaldehyde separation and removal system.

DESCRIPTION OF EMBODIMENTS

The method for producing acetic acid according to the present invention includes: a carbonylation reaction step of reacting methanol with carbon monoxide in a reaction vessel in the presence of a catalyst system containing a metal catalyst and methyl iodide as well as acetic acid, methyl acetate, and water to produce acetic acid; a separation step of using one or more evaporators and/or distillation columns to separate the reaction mixture obtained in the carbonylation reaction step into a stream containing the metal catalyst, an acetic acid stream rich in acetic acid, and a stream more enriched with a lower boiling point component than the acetic acid stream; an acetic acid distillation step, optionally included in the separation step, of distilling the acetic acid stream to purify the acetic acid; and an adsorptive removal step of treating the purified acetic acid stream obtained in the acetic acid distillation step with an ion exchange resin. In this method, the acetic acid distillation step has at least one distillation step of carrying out the purification of the acetic acid stream under conditions of a column bottom temperature of the distillation column of less than 175° C., a nickel base alloy or zirconium is used as a material of the distillation column in the distillation step, and the metal ion concentrations in the charging mixture of the distillation column in the distillation step are controlled such that the iron ion concentration is less than 10,000 ppb by mass, the chromium ion concentration is less than 5,000 ppb by mass, the nickel ion concentration is less than 3,000 ppb by mass, and the molybdenum ion concentration is less than 2,000 ppb by mass. It is preferred that the zinc ion concentration in the charging mixture of the dehydration column be less than 1,000 ppb by mass. Note that the charging mixture of the distillation column refers to the entire stream fed to the distillation column, and includes at least a part of the acetic acid stream sent from a distillation column immediately preceding that distillation column (e.g., if the immediately preceding distillation column is the distillation column at the lower boiling point component removal step, the above-mentioned first acetic acid stream). The charging mixture may also include a stream (e.g., a recycle stream from a downstream step) other than the acetic acid stream (e.g., the first acetic acid stream). The catalyst system may further include an ionic iodide.

The separation step preferably has, for example, an evaporation step of separating the reaction mixture obtained in the carbonylation reaction step into a vapor stream and a residual liquid stream in an evaporator, a lower boiling point component removal step of separating the vapor stream by distillation into an overhead stream rich in a lower boiling point component and a first acetic acid stream rich in acetic acid, and a dehydration step of separating the first acetic acid stream by distillation into an overhead stream rich in water and a second acetic acid stream more enriched with acetic acid than the first acetic acid stream.

The separation step may comprise, instead of the above-mentioned evaporation step and the lower boiling point component removal step, a step (an evaporative lower boiling point component removal step) of separating the reaction mixture obtained in the carbonylation reaction step into a stream containing the catalyst, an overhead stream rich in a lower boiling point component, and a first acetic acid stream rich in acetic acid. Further, the separation step may also comprise, instead of the above-mentioned lower boiling point component removal step and the dehydration step, a lower boiling point component removal step that also comprises the above-mentioned dehydration step (a so-called lower boiling point component removal and dehydration step), namely, a step of separating the vapor stream by distillation into an overhead stream rich in a lower boiling point component and a dehydrated acetic acid stream having a water concentration equal to that of the second acetic acid stream. Therefore, the evaporative lower boiling point component removal step may be a step also comprising the function of the above-mentioned dehydration step (an evaporative lower boiling point component removal and dehydration step). The acetic acid stream rich in acetic acid obtained from the lower boiling point component removal and dehydration step and the evaporative lower boiling point component removal and dehydration step corresponds to the above-mentioned second acetic acid stream.

The above-mentioned acetic acid distillation step may be a step included in the separation step or a step provided separately from the separation step. When the acetic acid distillation step is included in the separation step, the dehydration step, the lower boiling point component removal and dehydration step, and the evaporative lower boiling point component removal and dehydration step are included in the "acetic acid distillation step" of the present invention. Examples of the acetic acid distillation step provided separately from the separation step include the higher boiling point component removal step and the distillation step in a product column, which are described later.

The nickel base alloy is an alloy based on nickel. Examples thereof may include Hastelloy (Hastelloy B2, Hastelloy C, etc.), Monel, Inconel, Incoloy, and the like.

The iron ions, chromium ions, nickel ions, and molybdenum ions mentioned above are metal ions produced by corrosion of the apparatus (i.e., are corroded metal ions). On the other hand, the zinc ions are derived from zinc ions contained as impurities in the methanol used as a reaction raw material.

In the method for producing acetic acid according to the present invention, the acetic acid distillation step includes a distillation step in which the column bottom temperature of the distillation column is less than 175° C. (e.g., 173° C. or less). The distillation step in which the column bottom temperature of the distillation column is lower than 175° C. (e.g., 173° C. or less) is sometimes referred to as "distillation step (A)". The column bottom temperature refers to the temperature of the column bottom liquid. When purifying acetic acid by distilling an acetic acid stream containing acetic acid and an impurity having a higher boiling point than that of acetic acid, by setting the column bottom temperature of the distillation column to less than 175° C. (e.g., 173° C. or less), corrosion of the distillation column apparatus can be significantly suppressed. If the column bottom temperature of the distillation column is 175° C. or more, the corrosion rate of stainless steel and some nickel base alloys is fast even in the absence of acetate salts, acetic anhydride, and propionic acid in the column bottom liquid, showing that those materials are not suitable as the material of the distillation column apparatus.

By employing a nickel base alloy or zirconium, which has a higher corrosion resistance than a nickel base alloy, for the material of the distillation column in the acetic acid distillation step, corrosion of the apparatus by the hydrogen iodide or the acetic acid produced by the reaction system and included in the charging mixture of the distillation column and the resultant elution of corroded metal ions can be greatly suppressed. Further, by setting the column bottom temperature of the distillation column to less than 175° C. (e.g., 173° C. or less), corrosion of the distillation column can be significantly suppressed. Therefore, controlling the column bottom temperature of the distillation column in distillation step (A), controlling the amount of specific metal ions flowing into the distillation column, and suppressing the elution of the specific metal ions in the distillation column enable the concentration of the specific metal ions in the purified acetic acid obtained at the distillation column to be greatly reduced. As a result, the amount of the specific metal ions flowing to the subsequent adsorptive removal step can be reduced, and the life of the silver-substituted ion exchange resin (IER) used in that step can be greatly improved. Further, as a consequence of that, the metal ion concentrations in the purified acetic acid obtained in the adsorptive removal step can be reduced, and high-quality product acetic acid can be produced for a long time without exchanging the IER for a long period of time. When stainless steel, for example, is employed as the material of the distillation column, the inner portions of the distillation column are corroded by hydrogen iodide and acetic acid. When the column bottom temperature of the distillation column is 175° C. or more, corrosion of the inner portions of the distillation column proceeds even when there is no acetic acid salt (acetate salt), acetic anhydride, or propionic acid in the column bottom liquid. As a result, a large amount of corroded metals, such as iron, chromium, nickel, molybdenum, and the like, become mixed in the purified acetic acid, which causes the life of the IER used in the subsequent steps to be reduced. Further, when the concentrations of the specific metal ions in the charging mixture of the distillation column are higher than the above-described ranges as well, the metal concentrations in the above-mentioned purified acetic acid increase, and as a result the life of the IER used in subsequent steps is shortened.

It is preferred that the iron ion concentration in the charging mixture of the distillation column in distillation step (A) be less than 9,000 ppb by mass, more preferably less than 5,000 ppb by mass, further preferably less than 3,000 ppb by mass, particularly preferably less than 1,500 ppb by mass, and especially less than 800 ppb by mass (e.g., less than 400 ppb by mass). It is preferred that the chromium ion concentration in the charging mixture be less than 4,000 ppb by mass, more preferably less than 2,500 ppb by mass, further preferably less than 1,500 ppb by mass, particularly preferably less than 750 ppb by mass, and especially less than 400 ppb by mass (e.g., less than 200 ppb by mass). It is preferred that the nickel ion concentration in the charging mixture be less than 2,500 ppb by mass, more preferably less than 2,000 ppb by mass, further preferably less than 1,000 ppb by mass, particularly preferably less than 500 ppb by mass, and especially less than 250 ppb by mass (e.g., less than 150 ppb by mass). It is preferred that the molybdenum ion concentration in the charging mixture be less than 1,700 ppb by mass, more preferably less than 1,200 ppb by mass, further preferably less than 700 ppb by mass, particularly preferably less than 350 ppb by mass, and especially less than 170 ppb by mass. Further, it is preferred that the zinc ion concentration in the charging mixture be less than 800 ppb by mass, more preferably less than 650 ppb by mass, further preferably less than 500 ppb by mass, particularly preferably less than 410 ppb by mass, and especially less than 200 ppb by mass.

Examples of the method for controlling the concentrations of the specific metal ions in the charging mixture of the distillation column in distillation step (A) to be within the above-described specific ranges may include: (i) employing a metal having high corrosion resistance, such as a nickel base alloy or zirconium, as the material of the charging pipe to the distillation column; (ii) providing an ion exchange resin (in particular, a cation exchange resin) column (or vessel) for adsorptive removal of the specific metal ions at a suitable position between an outlet of the reaction vessel and an inlet of the distillation column; and (iii) using methanol having a very low metal ion content (e.g., zinc ion content) as the methanol to be fed to the reaction vessel. For example, because water, hydrogen iodide, and acetic acid are present in the charging mixture of the distillation column in the dehydration step (hereinafter, sometimes also referred to as "dehydration column"), the charging pipe to the dehydration column tends to corrode. However, by employing a metal having high corrosion resistance, such as a nickel base alloy or zirconium, for the material of the charging pipe, corrosion of the inner portions of the charging pipe and the resultant elution of corroded metal ions into the dehydration column charging mixture can be suppressed, which enables the metal ion concentrations in the dehydration column charging mixture to be reduced. Further, by providing an ion exchange resin treatment column (or vessel) for adsorptive removal of the specific metal ions at a suitable position between an outlet of the reaction vessel and an inlet of the dehydration column, the metal ions that have flowed along a path from the reaction system to immediately before the ion exchange resin treatment column (or vessel) or the metal ions that have been generated in the path can be removed, and the concentrations of the above-mentioned specific metal ions in the charging mixture to the dehydration column and a subsequent distillation column (e.g., distillation column in the higher boiling point component removal step) can be reduced to the above-described specific ranges. In addition, the inner surfaces of the tanker and the tank to be used for transporting and storing the methanol are coated with an inorganic zinc based coating material in order to prevent iron rust from occurring when drying. However, the zinc in the coating material elutes into the methanol during long-term transportation and storage. Therefore, methanol that is distributed on the market often contains zinc. This zinc is also a factor in reducing the life of the silver-substituted ion exchange resin (IER) used in the adsorptive removal step. Therefore, as the methanol to be used as a raw material in the reaction system, it is preferred that methanol containing as little zinc ions as possible be used. For methanol having a high zinc ion content, it is preferred that such methanol be fed to the reaction system after reducing the zinc ion concentration by, for example, treating with a cation exchange resin. The zinc ion concentration in the raw material methanol used in the reaction system is, for example, less than 10 ppm by mass, preferably less than 1 ppm by mass, further preferably less than 500 ppb by mass, and particularly preferably less than 100 ppm by mass. As described above, the zinc ions derived from the raw material methanol can be removed by providing an ion exchange resin (in particular, a cation exchange resin) column (or vessel) at a suitable position between an outlet of the reaction vessel and an inlet of the dehydration column.

The column bottom temperature of the distillation column in the distillation step (A) is preferably 173° C. or less (e.g., less than 173° C.), more preferably 172° C. or less, more preferably 170° C. or less, particularly preferably 168° C. or less, and especially 165° C. or less. If the column bottom temperature of the distillation column is 165° C. or less, and particularly 164° C. or less, corrosion of the inside portions of the distillation column can be suppressed more even if a considerable amount of acetate salts, acetic anhydride, and propionic acid is present in the column bottom liquid. Further, by setting the column bottom temperature of the distillation column to 163° C. or less, and particularly 162° C. or less, corrosion of the inside portions of the distillation column can be significantly suppressed. The lower limit of the column bottom temperature is, for example, 125° C., preferably 130° C., and more preferably 135° C.

The column top temperature of the distillation column in the distillation step (A) is, for example, less than 170° C., preferably 168° C. or less, more preferably 167° C. or less (e.g., less than 167° C.), even more preferably less than 165° C., still even more preferably less than 163° C., particularly preferably less than 161° C., and especially preferably less than 160° C. The lower limit of the column top temperature of the distillation column is, for example, 90° C., preferably 100° C., and more preferably 110° C.

The acetic acid distillation step has at least one distillation step in which the acetic acid concentration in the acetic acid stream (i.e., the charging mixture of the distillation column) to be distilled is 97% by mass or more, and in all such steps, it is preferable to carry out the distillation of the acetic acid stream in the distillation column under conditions of a column bottom temperature of less than 175° C. (i.e., distillation step (A)).

When the number of plates between the distillation column (particularly the dehydration column) in the distillation step (A) feeding plate and the column top vapor withdrawal plate is small, entrainment causes corroded metals in the charging mixture to flow out from the column top, and be recycled in the reaction system, for example. Therefore, although the metal concentrations in the purified acetic acid decrease, the originally intended concentration and separation efficiency of the water is reduced. As a result, it is preferred that the plate spacing (number of plates) between the charging mixture feeding plate (feeding plate) and the column top vapor withdrawal plate of the distillation column (particularly the dehydration column) be, in terms of actual plates, not less than 1 plate, more preferably not less than 3 plates, further preferably not less than 5 plates, and particularly preferably not less than 8 plates (among other things, not less than 10 plates).

The charging mixture of the distillation column in the distillation step (A) contains acetic acid and an impurity having a boiling point higher than that of acetic acid, and preferably contains acetic acid as a main component. The acetic acid concentration in the charging mixture is preferably 90% by mass or more (e.g., 95% by mass or more), more preferably 97% by mass or more, even more preferably 98% by mass or more, and particularly preferably 99% by mass or more.

The impurity having a higher boiling point than that of acetic acid is not particularly limited. However, in particular, when at least one compound selected from the group consisting of acetate salts, acetic anhydride, and propionic acid is included as the higher boiling point impurity, large effect can be obtained. Examples of the acetate salts include an alkali metal acetate such as potassium acetate, and the like.

The acetate salt concentration in the column bottom liquid of the distillation column (particularly the dehydration column) in the distillation step (A) is, for example, 34% by mass or less (e.g., 30% by mass or less), preferably 23% by mass or less (e.g., 15% by mass or less), more preferably 13% by mass or less (e.g., 12% by mass or less), even more preferably 10% by mass or less (e.g., 5% by mass or less), particularly preferably 1% by mass or less (e.g., 0.5% by mass or less), and especially preferably 0.3% by mass or less (e.g., 0.1% by mass or less), and may even be 0.05% by mass or less or 0.01% by mass or less. The lower the acetate salt concentration in the column bottom liquid, the slower the corrosion rate. The lower limit of the acetate salt concentration in the column bottom liquid is, for example, 0 ppm by mass (or 1 ppm by mass). In the carbonylation process of a methanol method, as described above, an alkali such as potassium hydroxide is added to neutralize the highly corrosive hydrogen iodide produced as a by-product in the reaction system. The added alkali not only reacts with the hydrogen iodide, but also reacts with the acetic acid to produce an acetate salt (e.g., potassium acetate). The column bottom liquid of the distillation column may include metals such as iron, nickel, chromium, manganese, and molybdenum (hereinafter, sometimes also referred to as "corrosion metals") produced by corrosion of the apparatus, and other metals such as cobalt, zinc, and copper. The corrosion metal and other metals are sometimes collectively referred to as "corroded metals and the like". Acetate salts (metal acetates) are formed between a corroded metal and acetic acid in the column bottom liquid of the distillation column. When such a crude acetic acid solution containing an acetate salt is distilled, it accumulates at the column bottom of the distillation column. Therefore, the acetate salt concentration in the column bottom liquid of the distillation column can be adjusted by, for example, increasing or reducing the added amount of alkali or suppressing corrosion of the inside portions of the distillation column.

The acetic anhydride concentration in the column bottom liquid of the distillation column (particularly the dehydration column) in the distillation step (A) is, for example, 90% by mass or less (e.g. 80% by mass or less), preferably 74% by mass or less (e.g., 60% by mass or less), more preferably 45% by mass or less (e.g., 20% by mass or less), even more preferably 10% by mass or less (e.g., 5% by mass or less), particularly preferably 1% by mass or less (e.g., 0.5% by mass or less), and especially preferably 0.2% by mass or less (e.g., 0.1% by mass or less), and may even be 0.05% by mass or less, 0.02% by mass or less or 0.01% by mass or less. The lower the acetic anhydride concentration in the column bottom liquid, the slower the corrosion rate. The lower limit of the acetic anhydride concentration in the column bottom liquid is, for example, 0 ppm by mass (or 1 ppm by mass). The acetic anhydride concentration in the column bottom liquid of the distillation column can be adjusted by, for example, adding water to the pipes or apparatus positioned upstream of the distillation column or to the distillation column to hydrolyze the acetic anhydride.

The propionic acid concentration in the column bottom liquid of the distillation column (particularly the dehydration column) in the distillation step (A) is, for example, 90% by mass or less (e.g. 80% by mass or less), preferably 75% by mass or less (e.g., 65% by mass or less), more preferably 55% by mass or less (e.g., 35% by mass or less), even more preferably 29% by mass or less (e.g., 20% by mass or less), particularly preferably 10% by mass or less (e.g., 5% by mass or less), and especially preferably 3% by mass or less (e.g., 1% by mass or less), and may even be 0.1% by mass or less, 0.05% by mass or less, or 0.03% by mass or less. The lower the propionic acid concentration in the column bottom liquid, the slower the corrosion rate. The lower limit of the propionic acid concentration in the column bottom liquid is, for example, 0 ppm by mass (or 1 ppm by mass). The concentration of propionic acid in the column bottom liquid of the distillation column can be reduced by, for example, changing the reaction conditions to reduce the amount of propionic acid produced as by-products, or during the recycling of a part of the process liquid to the reaction system, separating and removing acetaldehyde, which is a cause of propionic acid by-product production, from the process liquid and then recycling the resultant process liquid to the reaction system, or providing a distillation column or an evaporator (propionic acid removal column) for separating and removing propionic acid upstream of the distillation column.

The column bottom pressure of the distillation column (particularly the dehydration column) in the distillation step (A) is appropriately adjusted in accordance with the desired column bottom temperature and column bottom liquid composition. The column bottom pressure is, for example, less than 0.255 MPaG, preferably less than 0.24 MPaG, more preferably less than 0.23 MPaG, and particularly preferably less than 0.21 MPaG. Here, "G" indicates gauge pressure. Since the boiling point becomes higher as the concentration of the higher boiling point impurity in the column bottom liquid becomes higher, in order to obtain the desired column bottom temperature, it is necessary to lower the column bottom pressure more when the concentration of the higher boiling point impurity in the column bottom liquid is higher. The lower the column bottom pressure, the lower the column bottom temperature and the lower the corrosiveness, but if the column bottom pressure is low, the gas density decreases, so in order to maintain a constant acetic acid production amount, the column diameter and the like of the distillation column needs to be increased, which is economically disadvantageous. Therefore, the lower limit of the column bottom pressure of the distillation column is, for example, 0.01 MPaG, preferably 0.02 MPaG, more preferably 0.03 MPaG, and particularly preferably 0.05 MPaG. According to the present invention, since the column bottom temperature is adjusted to a specific value or less, acetic acid can be purified by distillation while preventing corrosion of the apparatus even under pressure. Therefore, the present invention is particularly useful when distillation is carried out under pressure to increase the production efficiency of the acetic acid.

Thus, in the present invention, because a specific material is employed for the material of the distillation column (particularly the dehydration column) in the distillation step (A), the column bottom temperature of the distillation column is set to less than 175° C., and the concentrations of specific metal ions in the distillation column charging mixture are controlled to be not more than certain values, the metal ion concentrations in the acid streams (e.g., the second acetic acid stream) obtained as a side stream or a bottom stream of the distillation column, can be reduced. The iron ion concentration in the acetic acid streams (e.g., the second acetic acid stream) is, for example, less than 21,000 ppb by mass, preferably less than 16,000 ppb by mass, more preferably less than 6,000 ppb by mass, further preferably less than 2,000 ppb by mass, and particularly preferably less than 200 ppb by mass. The chromium ion concentration in the acetic acid streams (e.g., the second acetic acid stream) is, for example, less than 7,100 ppb by mass, preferably less than 5,000 ppb by mass, more preferably less than 3,000 ppb by mass, further preferably less than 1,000 ppb by mass, and particularly preferably less than 100 ppb by mass. The nickel ion concentration in the acetic acid streams (e.g., the second acetic acid stream) is, for example, less than 4,000 ppb by mass, preferably less than 3,000 ppb by mass, more preferably less than 1,800 ppb by mass, further preferably less than 700 ppb by mass, and particularly preferably less than 70 ppb by mass. The molybdenum ion concentration in the acetic acid streams (e.g., the second acetic acid stream) is, for example, less than 3,000 ppb by mass, preferably less than 2,500 ppb by mass, more preferably less than 1,500 ppb by mass, further preferably less than 500 ppb by mass, and particularly preferably less than 50 ppb by mass. The zinc ion concentration in the acetic acid streams (e.g., the second acetic acid stream) are, for example, less than 1,000 ppb by mass, preferably less than 850 ppb by mass, more preferably less than 710 ppb by mass, further preferably less than 410 ppb by mass, and particularly preferably less than 150 ppb by mass.

In the present invention, the type of distillation may be either batch type distillation or continuous type distillation, but continuous distillation is more preferable from the viewpoint of production efficiency and the like.

In one preferred aspect of the present invention, in a distillation column having a nickel base alloy or zirconium as a material and having a plate spacing between a charging mixture feeding plate and a column top vapor withdrawal plate of not less than one plate in terms of actual plates (the theoretical number of plates being, for example, not less than 0.5), an overhead stream rich in water and purified acetic acid having an iron ion concentration of less than 21,000 ppb by mass, a chromium ion concentration of less than 7,100 ppb by mass, a nickel ion concentration of less than 4,000 ppb by mass, a molybdenum ion concentration of less than 3,000 ppb by mass, and a zinc ion concentration of less than 1,000 ppb by mass are obtained by feeding crude acetic acid having an iron ion concentration of less than 10,000 ppb by mass, a chromium ion concentration of less than 5,000 ppb by mass, a nickel ion concentration of less than 3,000 ppb by mass, a molybdenum ion concentration of less than 2,000 ppb by mass, a zinc ion concentration of less than 1,000 ppb by mass, a hexyl iodide concentration of less than 510 ppb by mass, and an acetic acid concentration of not less than 80% by mass into the charging mixture feeding plate through a charging pipe having a nickel base alloy or zirconium as a material, and conducting distillation under conditions of a column bottom temperature of less than 175° C.

Hereinafter, one embodiment of the present invention will be described. FIG. 1 is one example of an acetic acid production flow diagram (carbonylation process of a methanol method) showing one embodiment of the present invention. An acetic acid production apparatus associated with this acetic acid production flow has a reaction vessel 1, an evaporator 2, a distillation column 3, a decanter 4, a distillation column 5, a distillation column 6, an ion exchange resin column 7, a scrubber system 8, an acetaldehyde separation and removal system 9, condensers 1a, 2a, 3a, 5a, and 6a, a heat exchanger 2b, reboilers 3b, 5b, and 6b, lines 11 to 56, and a pump 57 and is configured to be capable of continuously producing acetic acid. In the method for producing acetic acid according to the present embodiment, a reaction step, an evaporation step (flash step), a first distillation step, a second distillation step, a third distillation step, and an adsorptive removal step are performed in the reaction vessel 1, the evaporator 2, the distillation column 3, the distillation column 5, the distillation column 6, and the ion exchange resin column 7, respectively. The first distillation step is also referred to as a lower boiling point component removal step, the second distillation step is also referred to as a dehydration step, and the third distillation step is also referred to as a higher boiling point component removal step. The second distillation step and the third distillation step are included in the "acetic acid distillation step" in the present invention. In the present invention, the steps are not limited to those described above and may exclude, particularly, equipment of the acetaldehyde separation and removal system 9 (acetaldehyde removal column, etc.). As mentioned later, a product column may be disposed downstream of the ion exchange resin column 7. This product column is also included in the "acetic acid distillation step" in the present invention.

The reaction vessel 1 is a unit for performing the reaction step. This reaction step is a step for continuously producing acetic acid through a reaction (methanol carbonylation reaction) represented by the chemical formula (1) given below. In a steady operation state of the acetic acid production apparatus, for example, a reaction mixture under stirring with a stirrer is present in the reaction vessel 1. The reaction mixture contains methanol and carbon monoxide which are raw materials, a metal catalyst, a co-catalyst, water, a production target acetic acid, and various by-products, and a liquid phase and a gaseous phase are in equilibrium.

$$CH_3OH + CO \rightarrow CH_3COOH \qquad (1)$$

The raw materials in the reaction mixture are methanol in a liquid state and carbon monoxide in a gaseous state. Methanol is continuously fed at a predetermined flow rate to the reaction vessel 1 from a methanol reservoir (not shown) through the line 11. As described above, the methanol that is distributed on the market often contains zinc. This zinc is also a factor in reducing the life of the silver-substituted ion exchange resin (IER) used in the subsequent adsorptive removal step. Therefore, regarding methanol that contains a large amount of zinc, it is preferred that before such methanol be used in the reaction, the zinc ion concentration in the methanol is reduced by treating the methanol with a cation exchange resin in advance.

Carbon monoxide is continuously fed at a predetermined flow rate to the reaction vessel 1 from a carbon monoxide reservoir (not shown) through the line 12. The carbon monoxide is not necessarily required to be pure carbon monoxide and may contain, for example, other gases such as nitrogen, hydrogen, carbon dioxide, and oxygen, in a small amount (e.g., not more than 5% by mass, preferably not more than 1% by mass).

The metal catalyst in the reaction mixture promotes the carbonylation reaction of methanol, and, for example, a rhodium catalyst or an iridium catalyst can be used. For example, a rhodium complex represented by the chemical formula $[Rh(CO)_2I_2]^-$ can be used as the rhodium catalyst. For example, an iridium complex represented by the chemical formula $[Ir(CO)_2I_2]^-$ can be used as the iridium catalyst. A metal complex catalyst is preferred as the metal catalyst. The concentration (in terms of the metal) of the catalyst in the reaction mixture is, for example, 200 to 5000 ppm by mass, preferably 400 to 2000 ppm by mass, with respect to the whole liquid phase of the reaction mixture.

The co-catalyst is, for example, an iodide for assisting the action of the catalyst mentioned above, and, for example, methyl iodide or an ionic iodide is used. The methyl iodide can exhibit the effect of promoting the catalytic effect of the catalyst mentioned above. The concentration of the methyl iodide is, for example, 1 to 20% by mass with respect to the whole liquid phase of the reaction mixture. The ionic iodide is an iodide that generates iodide ions in a reaction solution (particularly, an ionic metal iodide) and can exhibit the effect of stabilizing the catalyst mentioned above and the effect of suppressing side reaction. Examples of the ionic iodide include alkali metal iodides such as lithium iodide, sodium iodide, and potassium iodide. The concentration of the ionic iodide in the reaction mixture is, for example, 1 to 25% by mass, preferably 5 to 20% by mass, with respect to the whole liquid phase of the reaction mixture. Further, for example, when an iridium catalyst and the like are used, as a co-catalyst, a ruthenium compound or an osmium compound may also be used. The amount of such compounds used is, in total, for example, with respect to one mole of iridium (in terms of the metal), 0.1 to 30 moles (in terms of the metal), and is preferably 0.5 to 15 moles (in terms of the metal).

Water in the reaction mixture is a component necessary for generating acetic acid in the reaction mechanism of the methanol carbonylation reaction and is also a component necessary for solubilizing a water-soluble component in the reaction system. The concentration of water in the reaction mixture is, for example, 0.1 to 15% by mass, preferably 0.8 to 10% by mass, more preferably 1 to 6% by mass, further preferably 1.5 to 4% by mass, with respect to the whole liquid phase of the reaction mixture. The water concentration is preferably not more than 15% by mass for pursuing efficient acetic acid production by reducing energy required for the removal of water in the course of purification of acetic acid. In order to control the water concentration, water may be continuously fed at a predetermined flow rate to the reaction vessel 1.

The acetic acid in the reaction mixture includes acetic acid fed in advance into the reaction vessel 1 before operation of the acetic acid production apparatus, and acetic acid generated as a main product of the methanol carbonylation reaction. Such acetic acid can function as a solvent in the reaction system. The concentration of the acetic acid in the reaction mixture is, for example, 50 to 90% by mass, preferably 60 to 80% by mass, with respect to the whole liquid phase of the reaction mixture.

Examples of the main by-products contained in the reaction mixture include methyl acetate. This methyl acetate may be generated through the reaction between acetic acid and methanol. The concentration of the methyl acetate in the reaction mixture is, for example, 0.1 to 30% by mass, preferably 1 to 10% by mass, with respect to the whole liquid phase of the reaction mixture. Another example of the by-products contained in the reaction mixture includes hydrogen iodide. This hydrogen iodide is inevitably generated under the reaction mechanism of the methanol carbonylation reaction in the case where the catalyst or the co-catalyst as mentioned above is used. The concentration of the hydrogen iodide in the reaction mixture is, for example, 0.01 to 2% by mass with respect to the whole liquid phase of the reaction mixture. Other examples of the by-products include hydrogen, methane, carbon dioxide, acetaldehyde, crotonaldehyde, 2-ethyl crotonaldehyde, dimethyl ether, alkanes, formic acid, and propionic acid, and alkyl iodides such as hexyl iodide and decyl iodide. The concentration of hexyl iodide is, for example, 0.1 to 10,000 ppb by mass, normally 0.5 to 1,000 ppb by mass, and often 1 to 100 ppb by mass (e.g., 2 to 50 ppb by mass) with respect to the whole liquid phase of the reaction mixture. Also, the reaction mixture may contain a metal, such as iron, nickel, chromium, manganese, or molybdenum, generated by the corrosion of the apparatus (hereinafter, sometimes referred to as "corrosion metal"), and other metals such as cobalt, zinc, and copper. The corrosion metal and other metals are also collectively referred to as a "corroded metals and the like".

In the reaction vessel 1 where the reaction mixture as described above is present, the reaction temperature is set to, for example, 150 to 250° C. The reaction pressure as the total pressure is set to, for example, 2.0 to 3.5 MPa (absolute pressure), and the carbon monoxide partial pressure is set to, for example, 0.4 to 1.8 MPa (absolute pressure), preferably 0.6 to 1.6 MPa (absolute pressure), and further preferably 0.9 to 1.4 MPa (absolute pressure).

The vapor of a gaseous phase portion in the reaction vessel 1 during apparatus operation contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. This vapor can be withdrawn from the reaction vessel 1 through the line 13. The internal pressure of the reaction vessel 1 can be controlled by the adjustment of the amount of the vapor withdrawn, and, for example, the internal pressure of the reaction vessel 1 is kept constant. The vapor withdrawn from the reaction vessel 1 is introduced to the condenser 1a.

The condenser 1a separates the vapor from the reaction vessel 1 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 1a through the line 14 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 1a through the line 15. In the scrubber system 8, useful components (e.g., methyl iodide, water, methyl acetate, and acetic acid) are separated and recovered from the gaseous portion from the condenser 1a. In this separation and recovery, a wet method that is performed using an absorbing liquid for capturing the useful components in the gaseous portion is utilized in the present embodiment. An absorption solvent containing at least acetic acid and/or methanol is preferred as the absorbing liquid. The absorbing liquid may contain methyl acetate. For example, a condensate portion of a vapor from the distillation column 6 mentioned later can be used as the absorbing liquid. In the separation and recovery, a pressure swing adsorption method may be used. The separated and recovered useful components (e.g., methyl iodide) are introduced to the reaction vessel 1 from the scrubber system 8 through the recycle line 48 and recycled. A gas after the capturing of the useful components is discarded through the line 49. The gas discharged from the line 49 can be used as a CO source to be introduced to the bottom part of the evaporator 2 mentioned later or the residual liquid stream recycle lines 18 and 19. As for treatment in the scrubber system 8 and subsequent recycle to the reaction vessel 1 and discarding, the same holds true for gaseous portions described later that are fed to the scrubber system 8 from other condensers. For the production method of the present invention, it is preferred to have a scrubber step of separating offgas from the process into a stream rich in carbon monoxide and a stream rich in acetic acid by absorption treatment with an absorption solvent containing at least acetic acid.

In the reaction vessel 1 during apparatus operation, as mentioned above, acetic acid is continuously produced. The reaction mixture containing such acetic acid is continuously withdrawn at a predetermined flow rate from the reaction vessel 1 and introduced to the next evaporator 2 through the line 16.

The evaporator 2 is a unit for performing the evaporation step (flash step). This evaporation step is a step for separating the reaction mixture continuously introduced to the evaporator 2 through the line 16 (reaction mixture feed line), into a vapor stream (volatile phase) and a residual liquid stream (low volatile phase) by partial evaporation. The evaporation may be caused by reducing the pressure without heating the reaction mixture, or the evaporation may be caused by reducing the pressure while heating the reaction mixture. In the evaporation step, the temperature of the vapor stream is, for example, 100 to 260° C., preferably 120 to 200° C., and the temperature of the residual liquid stream is, for example, 80 to 200° C., preferably 100 to 180° C. The internal pressure of the evaporator is, for example, 50 to 1000 kPa (absolute pressure). The ratio between the vapor stream and the residual liquid stream to be separated in the evaporation step is, for example, 10/90 to 50/50 (vapor stream/residual liquid stream) in terms of a mass ratio. The vapor generated in this step contains, for example, methyl iodide, hydrogen iodide, water, methyl acetate, acetic acid, dimethyl ether, methanol, acetaldehyde, formic acid, propionic acid, and alkyl iodides such as ethyl iodide, propyl iodide, butyl iodide, hexyl iodide and decyl iodide and is continuously withdrawn to the line 17 (vapor stream discharge line) from the evaporator 2. A portion of the vapor stream withdrawn from the evaporator 2 is continuously introduced to the condenser 2a, and another portion of the vapor stream is continuously introduced to the next distillation column 3 through the line 21. The acetic acid concentration in the vapor stream is, for example, 40 to 85% by mass (preferably 50 to 85% by mass), and more preferably 50 to 75% by mass (e.g., 55 to 75% by mass). The methyl iodide concentration is, for example, 2 to 50% by mass (preferably 5 to 30%). The water concentration is, for example, 0.2 to 20% by mass (preferably 1 to 15% by mass). The methyl acetate concentration is, for example, 0.2 to 50% by mass (preferably 2 to 30% by mass). The hexyl iodide concentration in the vapor stream is, for example, 0.1 to 10,000 ppb by mass, normally 0.5 to 1,000 ppb by mass, and often 1 to 100 ppb by mass (e.g., 2 to 50 ppb by mass). The residual liquid stream generated in this step contains, for example, the catalyst and the co-catalyst (methyl iodide, lithium iodide, etc.) contained in the reaction mixture, and water, methyl acetate, acetic acid, formic acid, and propionic acid remaining without being volatilized in this step, and is continuously introduced to the heat exchanger 2b from the evaporator 2 through the line 18 using the pump 57. The heat exchanger 2b cools the residual liquid stream from the evaporator 2. The cooled residual liquid stream is continuously introduced to the reaction vessel 1 from the heat exchanger 2b through the line 19 and recycled. The line 18 and the line 19 are collectively referred to as residual liquid stream recycle lines. The acetic acid concentration of the residual liquid stream is, for example, 55 to 90% by mass, preferably 60 to 85% by mass.

The condenser 2a separates the vapor stream from the evaporator 2 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 2a through the lines 22 and 23 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 2a through the lines 20 and 15. Since the reaction to produce acetic acid in the reaction step mentioned above is an exothermic reaction, a portion of heat accumulated in the reaction mixture is transferred to the vapor generated from the reaction mixture in the evaporation step (flash step). The condensate portion generated by the cooling of this vapor in the condenser 2a is recycled to the reaction vessel 1. Specifically, in this acetic acid production apparatus, heat generated through the methanol carbonylation reaction is efficiently removed in the condenser 2a.

The distillation column 3 is a unit for performing the first distillation step and serves as the so-called lower boiling point component removal column in the present embodiment. The first distillation step is the step of subjecting the vapor stream continuously introduced to the distillation column 3 to distillation treatment to separate and remove lower boiling point components. More specifically, in the first distillation step, the vapor stream is separated by distillation into an overhead stream rich in at least one lower boiling point component selected from methyl iodide and acetaldehyde, and an acetic acid stream rich in acetic acid. The distillation column 3 consists of, for example, a distillation column such as a plate column or a packed column. In the case of adopting a plate column as the distillation column 3, the theoretical number of plates thereof is, for example, 5 to 50, and the reflux ratio is, for example, 0.5 to 3000 according to the theoretical number of plates. In the inside of the distillation column 3, the column top pressure is set to, for example, 80 to 160 kPaG, and the column bottom pressure is higher than the column top pressure and is set to, for example, 85 to 180 kPaG. In the inside of the distillation column 3, the column top temperature is, for example, a temperature of lower than the boiling point of acetic acid at the set column top pressure and is set to 90 to 130° C., and the column bottom temperature is, for example, a temperature of not less than the boiling point of acetic acid at the set column bottom pressure and is set to 120 to 165° C. (preferably 125 to 160° C.).

The vapor stream from the evaporator 2 is continuously introduced to the distillation column 3 through the line 21. From the column top of the distillation column 3, a vapor as the overhead stream is continuously withdrawn to the line 24. From the column bottom of the distillation column 3, a bottom fraction is continuously withdrawn to the line 25. 3b denotes a reboiler. From the height position between the column top and the column bottom of the distillation column 3, the acetic acid stream (first acetic acid stream; liquid) as a side stream is continuously withdrawn through the line 27.

The vapor withdrawn from the column top of the distillation column 3 contains a larger amount of components having a lower boiling point (lower boiling point components) than that of acetic acid as compared with the bottom fraction and the side stream from the distillation column 3 and contains, for example, methyl iodide, hydrogen iodide, water, methyl acetate, dimethyl ether, methanol, acetaldehyde, and formic acid. This vapor also contains acetic acid. Such a vapor is continuously introduced to the condenser 3a through the line 24.

The condenser 3a separates the vapor from the distillation column 3 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, and formic acid and is continuously introduced to the decanter 4 from the condenser 3a through the line 28. The condensate portion introduced to the decanter 4 is separated into an aqueous phase (upper phase) and an organic phase (methyl iodide phase; lower phase). The aqueous phase contains water and, for example, methyl iodide, hydrogen iodide, methyl acetate, acetic acid, dimethyl ether, methanol, acetaldehyde, and formic acid. The organic phase contains, for example, methyl iodide and, for example, hydrogen iodide, water, methyl acetate, acetic acid, dimethyl ether, methanol, acetaldehyde, and formic acid. In the present embodiment, a portion of the aqueous phase is refluxed to the distillation column 3 through the line 29, and another portion of the aqueous phase is introduced to the reaction vessel 1 through the lines 29, 30, and 23 and recycled. A portion of the organic phase is introduced to the reaction vessel 1 through the lines 31 and 23 and recycled. Another portion of the organic phase and/or a remaining portion of the aqueous phase is introduced to the acetaldehyde separation and removal system 9 through the lines 31 and 50 and/or the lines 30 and 51.

In the acetaldehyde separation and removal step using the acetaldehyde separation and removal system 9, acetaldehyde contained in the organic phase and/or the aqueous phase is separated and removed by a method known in the art, for example, distillation, extraction, or a combination thereof. The separated acetaldehyde is discharge to the outside of the apparatus through the line 53. The useful components (e.g., methyl iodide) contained in the organic phase and/or the aqueous phase are recycled to the reaction vessel 1 through the lines 52 and 23 and reused.

FIG. 2 is a schematic flow diagram showing one example of the acetaldehyde separation and removal system. According to this flow, in the case of treating, for example, the organic phase in the acetaldehyde separation and removal step, the organic phase is fed to a distillation column (first acetaldehyde removal column) 91 through a line 101 and separated by distillation into an overhead stream rich in acetaldehyde (line 102) and a residual liquid stream rich in methyl iodide (line 103). The overhead stream is condensed in a condenser 91a. A portion of the condensate is refluxed to the column top of the distillation column 91 (line 104), and the remaining portion of the condensate is fed to an extraction column 92 (line 105). The condensate fed to the extraction column 92 is subjected to extraction treatment with water introduced from a line 109. The extract obtained by the extraction treatment is fed to a distillation column (second acetaldehyde removal column) 93 through a line 107 and separated by distillation into an overhead stream rich in acetaldehyde (line 112) and a residual liquid stream rich in water (line 113). Then, the overhead stream rich in acetaldehyde is condensed in a condenser 93a. A portion of the condensate is refluxed to the column top of the distillation column 93 (line 114), and the remaining portion of the condensate is discharged to the outside of the system (line 115). The residual liquid stream rich in methyl iodide, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through a line 110. The liquid from the line 113 is usually discharged to the outside as water discharge. A gas that has not been condensed in the condenser 91a or 93a (line 106 or 116) is subjected to absorption treatment in the scrubber system 8 or discarded.

According to the flow of FIG. 2, in the case of treating the aqueous phase in the acetaldehyde separation and removal step, for example, the aqueous phase is fed to the distillation column (first acetaldehyde removal column) 91 through the line 101 and separated by distillation into an overhead stream rich in acetaldehyde (line 102) and a residual liquid stream rich in water (line 103). The overhead stream is condensed in the condenser 91a. A portion of the condensate is refluxed to the column top of the distillation column 91 (line 104), and the remaining portion of the condensate is fed to the extraction column 92 (line 105). The condensate fed to the extraction column 92 is subjected to extraction treatment with water introduced from the line 109. The extract obtained by the extraction treatment is fed to the distillation column (second acetaldehyde removal column) 93 through the line 107 and separated by distillation into an overhead stream rich in acetaldehyde (line 112) and a residual liquid stream rich in water (line 113). Then, the overhead stream rich in acetaldehyde is condensed in the condenser 93a. A portion of the condensate is refluxed to the column top of the distillation column 93 (line 114), and the remaining portion of the condensate is discharged to the outside of the system (line 115). The residual liquid stream rich in water, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through the line 110. The liquid from the line 113 is usually discharged to the outside as water discharge. A gas that has not been condensed in the condenser 91a or 93a (line 106 or 116) is subjected to absorption treatment in the scrubber system 8 or discarded.

The acetaldehyde derived from the process stream containing at least the water, the acetic acid (AC), the methyl iodide (MeI), and the acetaldehyde (AD) can also be separated and removed by use of extractive distillation, in addition to the method described above. For example, the organic phase and/or the aqueous phase (charging mixture) obtained by the separation of the process stream is fed to a distillation column (extractive distillation column). In addition, an extraction solvent (usually, water) is introduced to a concentration zone (e.g., space from the column top to the charging mixture feeding position) where methyl iodide and acetaldehyde in the distillation column are concentrated. A liquid (extract) dropped from the concentration zone is withdrawn as a side stream (side cut stream). This side stream is separated into an aqueous phase and an organic phase. The aqueous phase can be distilled to thereby discharge acetaldehyde to the outside of the system. In the case where a relatively large amount of water is present in the distillation column, the liquid dropped from the concentration zone may be withdrawn as a side stream without introducing the extraction solvent to the distillation column. For example, a unit (chimney tray, etc.) that can receive the liquid (extract) dropped from the concentration zone is disposed in this distillation column so that a liquid (extract) received by this unit can be withdrawn as a side stream. The extraction solvent introduction position is preferably superior to the charging mixture feeding position, more preferably near the column top. The side stream withdrawal position is preferably lower than the extraction solvent introduction position and higher than the charging mixture feeding position, in the height direction of the column. According to this method, acetaldehyde can be extracted with a high concentration from a concentrate of methyl iodide and the acetaldehyde using an extraction solvent (usually, water). In addition, the region between the extraction solvent introduction site and the side cut site is used as an extraction zone. Therefore, acetaldehyde can be efficiently extracted with a small amount of the extraction solvent. Therefore, for example, the number of plates in the distillation column can be drastically decreased as compared with a method of withdrawing an extract by extractive distillation from the column bottom of the distillation column (extractive distillation column). In addition, steam load can also be reduced. Furthermore, the ratio of methyl iodide to acetaldehyde (MeI/AD ratio) in a water extract can be decreased as compared with a method of combining the aldehyde removing distillation of FIG. 2 with water extraction using a small amount of an extraction solvent. Therefore, acetaldehyde can be removed under conditions that can suppress a loss of methyl iodide to the outside of the system. The acetaldehyde concentration in the side stream is much higher than the acetaldehyde concentration in the charging mixture and the bottom fraction (column bottom fraction). The ratio of acetaldehyde to methyl iodide in the side stream is larger than the ratio of acetaldehyde to methyl iodide in the charging mixture and the bottom fraction. The organic phase (methyl iodide phase) obtained by the separation of the side stream may be recycled to this distillation column. In this case, the recycle position of the organic phase obtained by the separation of the side stream is preferably lower than the side stream withdrawal position and preferably higher than the charging mixture feeding position, in the height direction of the column. A solvent miscible with the components (e.g., methyl acetate) constituting the organic phase obtained by the separation of the process stream may be introduced to this distillation column (extractive distillation column). Examples of the miscible solvent include acetic acid and ethyl acetate. The miscible solvent introduction position is preferably lower than the side stream withdrawal position and preferably higher than the charging mixture feeding position, in the height direction of the column. Also, the miscible solvent introduction position is preferably inferior to a recycle position in the case where the organic phase obtained by the separation of the side stream is recycled to this distillation column. The organic phase obtained by the separation of the side stream is recycled to the distillation column, or the miscible solvent is introduced to the distillation column, whereby the methyl acetate concentration in the extract withdrawn as the side stream can be decreased, and the methyl acetate concentration in the aqueous phase obtained by the separation of the extract can be lowered. Hence, the contamination of the aqueous phase with methyl iodide can be suppressed.

The theoretical number of plates of the distillation column (extractive distillation column) is, for example, 1 to 100, preferably 2 to 50, more preferably 3 to 30, further preferably 5 to 20. Acetaldehyde can be efficiently separated and removed by a smaller number of plates than 80 to 100 plates in a distillation column or an extractive distillation column for use in conventional acetaldehyde removal. The mass ratio between the flow rate of the extraction solvent and the flow rate of the charging mixture (the organic phase and/or the aqueous phase obtained by the separation of the process stream) (former/latter) may be selected from the range of 0.0001/100 to 100/100 and is usually 0.0001/100 to 20/100, preferably 0.001/100 to 10/100, more preferably 0.01/100 to 8/100, further preferably 0.1/100 to 5/100. The column top temperature of the distillation column (extractive distillation column) is, for example, 15 to 120° C., preferably 20 to 90° C., more preferably 20 to 80° C., further preferably 25 to 70° C. The column top pressure is, on the order of, for example, 0.1 to 0.5 MPa in terms of absolute pressure. Other conditions for the distillation column (extractive distillation column) may be the same as those for a distillation column or an extractive distillation column for use in conventional acetaldehyde removal.

FIG. 3 is a schematic flow diagram showing another example of the acetaldehyde separation and removal system using the extractive distillation described above. In this example, the organic phase and/or the aqueous phase (charging mixture) obtained by the separation of the process stream is fed to a middle part (position between the column top and the column bottom) of a distillation column 94 through a feed line 201, while water is introduced thereto from near the column top through a line 202 so that extractive distillation is performed in the distillation column 94 (extractive distillation column). A chimney tray 200 for receiving a liquid (extract) dropped from a concentration zone where methyl iodide and acetaldehyde in the column are concentrated is disposed superior to the charging mixture feeding position of the distillation column 94. In this extractive distillation, preferably the whole amount, of the liquid on the chimney tray 200 is withdrawn, introduced to a decanter 95 through a line 208, and separated. The aqueous phase (containing acetaldehyde) in the decanter 95 is introduced to a cooler 95*a* through a line 212 and cooled so that methyl iodide dissolved in the aqueous phase is separated into 2 phases in a decanter 96. The aqueous phase in the decanter 96 is fed to a distillation column 97 (acetaldehyde removal column) through a line 216 and distilled. The vapor at the column top is led to a condenser 97*a* through a line 217 and condensed. A portion of the condensate (mainly, acetaldehyde and methyl iodide) is refluxed to the column top of the distillation column 97, and the remaining portion is discarded or fed to a distillation column 98 (extractive distillation column) through a line 220. Water is introduced thereto from near the column top of the distillation column 98 through a line 222, followed by extractive distillation. The vapor at the column top is led to a condenser 98*a* through a line 223 and condensed. A portion of the condensate (mainly, methyl iodide) is refluxed to the column top, and the remaining portion is recycled to the reaction system through a line 226, but may be discharged to the outside of the system. Preferably the whole amount, of the organic phase (methyl iodide phase) in the decanter 95 is recycled to below the position of the chimney tray 200 of the distillation column 94 through lines 209 and 210. A portion of the aqueous phase of the decanter 95 and the organic phase of the decanter 96 are recycled to the distillation column 94 through lines 213 and 210 and lines 214 and 210, respectively, but may not be recycled. A portion of the aqueous phase of the decanter 95 may be utilized as an extraction solvent (water) in the distillation column 94. A portion of the aqueous phase of the decanter 96 may be recycled to the distillation column 94 through the line 210. In some cases (e.g., the case where methyl acetate is contained in the charging mixture), a solvent (acetic acid, ethyl acetate, etc.)

miscible with the components (e.g., methyl acetate) constituting the organic phase obtained by the separation of the process stream may be fed to the distillation column 94 through a line 215 to thereby improve distillation efficiency. The feeding position of the miscible solvent to the distillation column 94 is superior to the charging mixture feeding portion (junction of the line 201) and inferior to the junction of the recycle line 210. A bottom fraction of the distillation column 94 is recycled to the reaction system. A vapor at the column top of the distillation column 94 is led to a condenser 94a through a line 203 and condensed. The condensate is separated in a decanter 99. The organic phase is refluxed to the column top of the distillation column 94 through a line 206, while the aqueous phase is led to the decanter 95 through a line 207. A bottom fraction (water is a main component) of the distillation column 97 and a bottom fraction (water containing a small amount of acetaldehyde) of the distillation column 98 (extractive distillation column) are discharged to the outside of the system through lines 218 and 224, respectively, or recycled to the reaction system. A gas (line 211, 221, or 227) that has not been condensed in the condenser 94a, 97a, or 98a is subjected to absorption treatment in the scrubber system 8 or discarded.

FIG. 4 is a schematic flow diagram showing a further alternative example of the acetaldehyde separation and removal system using the extractive distillation described above. In this example, a condensate of a vapor from the column top of the distillation column 94 is led to a hold tank 100, and the whole amount thereof is refluxed to the column top of the distillation column 94 through the line 206. The other points are the same as in the example of FIG. 3.

FIG. 5 is a schematic flow diagram showing a further alternative example of the acetaldehyde separation and removal system using the extractive distillation described above. In this example, the whole amount of a liquid on the chimney tray 200 is withdrawn, directly introduced to the cooler 95a through the line 208 without the medium of the decanter 95, cooled, and fed to the decanter 96. The other points are the same as in the example of FIG. 4.

In FIG. 1 described above, the gaseous portion generated in the condenser 3a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 3a through the lines 32 and 15. For example, methyl iodide, hydrogen iodide, water, methyl acetate, acetic acid, dimethyl ether, methanol, acetaldehyde, and formic acid in the gaseous portion that has entered the scrubber system 8 are absorbed to an absorbing liquid in the scrubber system 8. The hydrogen iodide generates methyl iodide through reaction with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction withdrawn from the column bottom of the distillation column 3 contains a larger amount of components having a higher boiling point (higher boiling point components) than that of acetic acid as compared with the overhead stream and the side stream from the distillation column 3 and contains, for example, propionic acid, and the entrained catalyst and co-catalyst mentioned above. This bottom fraction also contains, for example, acetic acid, methyl iodide, methyl acetate, and water. In the present embodiment, a portion of such a bottom fraction is continuously introduced to the evaporator 2 through the lines 25 and 26 and recycled, and another portion of the bottom fraction is continuously introduced to the reaction vessel 1 through the lines 25 and 23 and recycled.

The first acetic acid stream continuously withdrawn as a side stream from the distillation column 3 is more enriched with acetic acid than the vapor stream continuously introduced to the distillation column 3. Specifically, the acetic acid concentration of the first acetic acid stream is higher than the acetic acid concentration of the vapor stream. The acetic acid concentration of the first acetic acid stream is, for example, 90 to 99.9% by mass, preferably 93 to 99% by mass. Also, the first acetic acid stream contains, in addition to acetic acid, for example, methyl iodide, hydrogen iodide, water, methyl acetate, dimethyl ether, methanol, acetaldehyde, formic acid, and propionic acid, and alkyl iodides such as ethyl iodide, propyl iodide, butyl iodide, hexyl iodide and decyl iodide. In the first acetic acid stream, the methyl iodide concentration is, for example, 8% by mass or less (e.g., 0.1 to 8% by mass), and preferably 0.2 to 5% by mass, the water concentration is, for example, 8% by mass or less (e.g., 0.1 to 8% by mass), and preferably 0.2 to 5% by mass, and the methyl acetate concentration is, for example, 8% by mass or less (e.g., 0.1 to 8% by mass), and preferably 0.2 to 5% by mass. The hexyl iodide concentration in the first acetic acid stream is, for example, 0.2 to 10,000 ppb by mass, normally 1 to 1,000 ppb by mass, and often 2 to 100 ppb by mass (e.g., 3 to 50 ppb by mass). The connection position of the line 27 to the distillation column 3 may be, as shown in the drawing, higher than the connection position of the line 21 to the distillation column 3 in the height direction of the distillation column 3, but may be lower than the connection position of the line 21 to the distillation column 3 or may be the same as the connection position of the line 21 to the distillation column 3. The first acetic acid stream from the distillation column 3 is continuously introduced at a predetermined flow rate to the next distillation column 5 through the line 27. Note that the first acetic acid stream withdrawn as a side stream of the distillation column 3 and the column bottom liquid of the distillation column 3 or vapor condensate of the column bottom portion of the distillation column 3 can be continuously introduced into the distillation column 6 (described later) directly without going through the distillation column 5 (the dehydration step). The material of the line 27 or the material of the distillation column 5 (at least the material of the portions in contact with the liquids and gases) may be stainless steel, but it is preferred that a metal having high corrosion resistance, such as a nickel base alloy and zirconium, be used in order to suppress corrosion of the pipes and the inner portions of the distillation column by hydrogen iodide and acetic acid.

To the first acetic acid stream flowing through the line 27, potassium hydroxide can be fed or added through the line 55 (potassium hydroxide introduction line). The potassium hydroxide can be fed or added, for example, as a solution such as an aqueous solution. Hydrogen iodide in the first acetic acid stream can be decreased by the feed or addition of potassium hydroxide to the first acetic acid stream. Specifically, the hydrogen iodide reacts with the potassium hydroxide to form potassium iodide and water. This can reduce the corrosion of an apparatus such as a distillation column ascribable to hydrogen iodide. In this process, the potassium hydroxide can be fed or added to an appropriate site where hydrogen iodide is present. The potassium hydroxide added during the process also reacts with acetic acid to form potassium acetate.

The distillation column 5 is a unit for performing the second distillation step and serves as the so-called dehydration column in the present embodiment. The second distillation step is a step for further purifying acetic acid by the distillation treatment of the first acetic acid stream continuously introduced to the distillation column 5. In the distillation column 5, as defined by the present invention, it is preferable to obtain purified acetic acid by distilling the first acetic acid stream fed via the line 27 under conditions of a column bottom temperature of less than 175° C. Further, as defined by the present invention, it is preferred that the material of the distillation column 5 (at least the material of the portions in contact with the liquids and gases) be a nickel base alloy or zirconium. By using such a material, corrosion of the inner portions of the distillation column by hydrogen iodide and acetic acid can be suppressed, and elution of corroded metal ions can also be suppressed.

The charging mixture of the distillation column 5 includes at least a part (line 27) of the first acetic acid stream, to which a stream other than the first acetic acid stream [e.g., a recycle stream from a downstream step (e.g., line 42)] may be added. Preferably, in the present invention, as the metal ion concentrations in the charging mixture of the distillation column 5, the iron ion concentration is less than 10,000 ppb by mass, the chromium ion concentration is less than 5,000 ppb by mass, the nickel ion concentration is less than 3,000 ppb by mass, and the molybdenum ion concentration is less than 2,000 ppb by mass. By employing the above-described specific material for the material of the distillation column 5, setting the column bottom temperature of the distillation column to less than 175° C., and controlling the metal ion concentrations in the charging mixture to the distillation column 5 within the above-described ranges, the corroded metal concentrations in the purified acetic acid obtained in this step can be remarkably reduced, the metal concentrations in the acetic acid fed to the subsequent adsorptive removal step can also be reduced, and the life of the silver-substituted ion exchange resin (IER) can be greatly improved. It is preferred that the iron ion concentration in the charging mixture of the distillation column 5 be less than 9,000 ppb by mass, more preferably less than 5,000 ppb by mass, further preferably less than 3,000 ppb by mass, particularly preferably less than 1,500 ppb by mass, and especially less than 800 ppb by mass (e.g., less than 400 ppb by mass). It is preferred that the chromium ion concentration in the charging mixture be less than 4,000 ppb by mass, more preferably less than 2,500 ppb by mass, further preferably less than 1,500 ppb by mass, particularly preferably less than 750 ppb by mass, and especially less than 400 ppb by mass (e.g., less than 200 ppb by mass). It is preferred that the nickel ion concentration in the charging mixture be less than 2,500 ppb by mass, more preferably less than 2,000 ppb by mass, further preferably less than 1,000 ppb by mass, particularly preferably less than 500 ppb by mass, and especially less than 250 ppb by mass (e.g., less than 150 ppb by mass). It is preferred that the molybdenum ion concentration in the charging mixture be less than 1,700 ppb by mass, more preferably less than 1,200 ppb by mass, further preferably less than 700 ppb by mass, particularly preferably less than 350 ppb by mass, and especially less than 170 ppb by mass. Further, the zinc ion concentration in the charging mixture is, for example, less than 1,000 ppb by mass, preferably less than 800 ppb by mass, more preferably less than 650 ppb by mass, further preferably less than 500 ppb by mass, particularly preferably less than 410 ppb by mass, and especially less than 200 ppb by mass. The hexyl iodide concentration in the charging mixture is, for example, 0.2 to 10,000 ppb by mass, normally 1 to 1,000 ppb by mass, and often 2 to 100 ppb by mass (e.g., 3 to 50 ppb by mass, and particularly 5 to 40 ppb by mass). The acetic acid concentration in the charging mixture of the distillation column 5 is, for example, 90% by mass or more (e.g., 95% by mass or more), more preferably 97% by mass or more, even more preferably 98% by mass or more, and particularly preferably 99% by mass or more. Further, the charging mixture of the distillation column 5 may contain at least one compound selected from the group consisting of an acetate salt, acetic anhydride, and propionic acid.

The distillation column 5 consists of, for example, a distillation column such as a plate column and a packed column. In the case of adopting a plate column as the distillation column 5, the theoretical number of plates thereof is, for example, 5 to 50, and the reflux ratio is, for example, 0.2 to 3,000 according to the theoretical number of plates.

In the inside of the distillation column 5 that is at the second distillation step, it is preferred that the column top pressure and the column bottom pressure be set in accordance with the column bottom liquid composition such that the column bottom temperature is less than 175° C. The column top pressure is set to, for example, 0.10 to 0.28 MPaG, preferably 0.15 to 0.23 MPaG, and further preferably 0.17 to 0.21 MPaG. The column bottom pressure is higher than the column top pressure, and is, for example, 0.13 to 0.31 MPaG, preferably 0.18 to 0.26 MPaG, and more preferably 0.20 to 0.24 MPaG. In the inside of the distillation column 5 that is at the second distillation step, the column top temperature is, for example, a temperature higher than the boiling point of water and lower than the boiling point of acetic acid at the set column top pressure, and is set to 110° C. or more and less than 170° C. The column top temperature is, for example, 168° C. or less, preferably 167° C. or less, more preferably less than 167° C., even more preferably less than 165° C., still even more preferably less than 163° C., particularly preferably less than 161° C., and especially preferably less than 160° C. The lower limit of the column top temperature is, for example, 90° C., preferably 100° C., and more preferably 110° C. The column bottom temperature is, for example, a temperature equal to or higher than the boiling point of acetic acid at the set column bottom pressure, and is set to 120° C. or more and less than 175° C. The column bottom temperature is preferably 173° C. or less (e.g., less than 173° C.), more preferably 172° C. or less (e.g., 170° C. or less), even more preferably 168° C. or less (e.g., 165° C. or less), particularly preferably 165° C. or less (e.g., 164° C. or less), and especially preferably 163° C. or less (e.g., 162° C. or less). Further, the lower limit of the column bottom temperature is, for example, 125° C., preferably 130° C., and more preferably 135° C. Setting the column bottom temperature of the dehydration column to less than 175° C. and the column top temperature to within the above range enables corrosion of the inner portions of the distillation column due to hydrogen iodide or acetic acid to be suppressed more, and elution of the corroded metal ions to be suppressed more.

In order to achieve a sufficient concentration and separation efficiency of water in the distillation column 5, it is preferred that the plate spacing (number of plates) between the charging mixture feeding plate (feeding plate) and the column top vapor withdrawal plate of the distillation column 5 be, in terms of actual plates, not less than 1 plate, more preferably not less than 3 plates, further preferably not less than 5 plates, and particularly preferably not less than 8 plates (among other things, not less than 10 plates).

A vapor as an overhead stream is continuously withdrawn to the line 33 from the column top of the distillation column 5. A bottom fraction is continuously withdrawn to the line 34 from the column bottom of the distillation column 5. 5b denotes a reboiler. A side stream (liquid or gas) may be continuously withdrawn to the line 34 from the height position between the column top and the column bottom of the distillation column 5.

The vapor withdrawn from the column top of the distillation column 5 contains a larger amount of components having a lower boiling point (lower boiling point components) than that of acetic acid as compared with the bottom fraction from the distillation column 5 and contains, for example, methyl iodide, hydrogen iodide, water, methyl acetate, acetic acid, dimethyl ether, methanol, acetaldehyde, and formic acid. Such a vapor is continuously introduced to the condenser 5a through the line 33.

The condenser 5a separates the vapor from the distillation column 5 into a condensate portion and a gaseous portion by cooling and partial condensation. The condensate portion contains, for example, water and acetic acid. A portion of the condensate portion is continuously refluxed to the distillation column 5 from the condenser 5a through the line 35. Another portion of the condensate portion is continuously introduced to the reaction vessel 1 from the condenser 5a through the lines 35, 36, and 23 and recycled. The gaseous portion generated in the condenser 5a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 5a through the lines 37 and 15. Hydrogen iodide in the gaseous portion that has entered the scrubber system 8 is absorbed to an absorbing liquid in the scrubber system 8. Methyl iodide is generated through the reaction of the hydrogen iodide with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction (or the side stream) withdrawn from the column bottom of the distillation column 5 contains a larger amount of components having a higher boiling point (higher boiling point components) than that of acetic acid as compared with the overhead stream from the distillation column 5, and contains, for example, acetic anhydride, propionic acid, acetate salts, iodide salts such as potassium iodide or metal iodides derived from the corroded metals and the like, and the entrained catalyst and co-catalyst mentioned above. Examples of the acetate salts include potassium acetate formed when an alkali, such as potassium hydroxide, is fed to the line 27 or the like. Another example is a metal acetate formed by acetic acid and a corroded metal and the like, such as a metal formed at and released from the inside wall of a member constituting this acetic acid production apparatus. Examples of iodide salts include potassium iodide formed when an alkali, such as potassium hydroxide, is fed to the line 27 or the like. This bottom fraction may also contain acetic acid. Such a bottom fraction is continuously introduced in the form of the second acetic acid stream to the next distillation column 6 through the line 34. The bottom fraction (or the side stream) withdrawn from the column bottom of the distillation column 5 contains the corroded metals and the like and compounds (iodide salts) of the corroded metals and the like and the iodine derived from corrosive iodine. In the present embodiment, such a bottom fraction is discharged outside the acetic acid production apparatus.

In the present invention, from the perspective of suppressing corrosion of the distillation column, it is more preferred that the concentrations of the acetate salts, propionic acid, iodide salts, and acetic anhydride in the column bottom liquid of the distillation column 5 each be lower. The acetate salt concentration in the column bottom liquid of the distillation column 5 is, for example, 0.1 ppm by mass to 34% by mass, preferably 1 ppm by mass to 10% by mass, more preferably 10 ppm by mass to 1% by mass (e.g., 20 ppm by mass to 0.5% by mass). The propionic acid concentration in the column bottom liquid of the distillation column 5 is, for example, 10 ppm by mass to 91% by mass (e.g., 10 ppm by mass to 90% by mass), preferably 50 ppm by mass to 75% by mass, more preferably 100 ppm by mass to 55% by mass, even more preferably 150 ppm by mass to 29% by mass, and particularly preferably 200 ppm by mass to 15% by mass. The iodide salt concentration in the column bottom liquid of the distillation column 5 is, for example, 0.01 ppb by mass to 1000 ppm by mass, preferably 0.1 ppb by mass to 500 ppm by mass, more preferably 0.5 ppb by mass to 100 ppm by mass, even more preferably 1 ppb by mass to 10 ppm by mass, and particularly preferably 2 ppb by mass to 1 ppm by mass. The acetic anhydride concentration in the column bottom liquid of the distillation column 5 is, for example, 90% by mass or less (e.g., 80% by mass or less or 50% by mass or less), preferably 0.1 ppm by mass to 10% by mass, more preferably 0.5 ppm by mass to 1% by mass, even more preferably 1 to 1000 ppm by mass, and particularly preferably 2 to 500 ppm by mass. The acetate salt concentration and the iodide salt concentration in the column bottom liquid of the distillation column 5 can be reduced by, for example, reducing the added amount of alkali used for neutralization of the hydrogen iodide, or making corrosion inside the distillation column more difficult to occur. The concentration of propionic acid in the column bottom liquid of the distillation column 5 can be reduced by, for example, changing the reaction conditions to reduce the amount of propionic acid produced as by-products in the reaction vessel, or during the recycling of a part of the process liquid to the reaction system, separating and removing acetaldehyde, which is a cause of propionic acid by-product production, from the process liquid and then recycling the resultant process liquid to the reaction system, or providing a distillation column or an evaporator (propionic acid removal column) for separating and removing propionic acid upstream of the distillation column 5. Further, the acetic anhydride concentration in the column bottom liquid of the distillation column 5 can also be reduced by, for example, adding water to the pipes or apparatus positioned upstream of the distillation column 5 or to the distillation column 5 to hydrolyze the acetic anhydride.

The second acetic acid stream is more enriched with acetic acid than the first acetic acid stream continuously introduced to the distillation column 5. Specifically, the acetic acid concentration of the second acetic acid stream is higher than the acetic acid concentration of the first acetic acid stream. The acetic acid concentration of the second acetic acid stream is, for example, 99.1 to 99.99% by mass as long as being higher than the acetic acid concentration of the first acetic acid stream. Also, the second acetic acid stream may contain, as described above, in addition to acetic acid, for example, propionic acid and hydrogen iodide. In the present embodiment, in the case of withdrawing a side stream, the withdrawal position of the side stream from the distillation column 5 is lower than the introduction position of the first acetic acid stream to the distillation column 5 in the height direction of the distillation column 5.

In the present invention, preferably, a specific material is employed for the material of the dehydration column, the column bottom temperature is set to a specific value or less, and the metal ion concentrations in the charging mixture of the dehydration column are set to a specific value or less, and hence the metal ion concentrations in the side stream of the dehydration column or the second acetic acid stream obtained as the bottom fraction can be remarkably reduced. The iron ion concentration in the second acetic acid stream is, for example, is less than 21,000 ppb by mass, preferably less than 16,000 ppb by mass, more preferably less than 6,000 ppb by mass, further preferably less than 2,000 ppb by mass, and particularly preferably less than 200 ppb by mass. The chromium ion concentration in the second acetic acid stream is, for example, less than 7,100 ppb by mass, preferably less than 5,000 ppb by mass, more preferably less than 3,000 ppb by mass, further preferably less than 1,000 ppb by mass, and particularly preferably less than 100 ppb by mass. The nickel ion concentration in the second acetic acid stream is, for example, less than 4,000 ppb by mass, preferably less than 3,000 ppb by mass, more preferably less than 1,800 ppb by mass, further preferably less than 700 ppb by mass, and particularly preferably less than 70 ppb by mass. The molybdenum ion concentration in the second acetic acid stream is, for example, less than 3,000 ppb by mass, preferably less than 2,500 ppb by mass, more preferably less than 1,500 ppb by mass, further preferably less than 500 ppb by mass, and particularly preferably less than 50 ppb by mass. The zinc ion concentration in the second acetic acid stream is, for example, less than 1,000 ppb by mass, preferably less than 850 ppb by mass, more preferably less than 710 ppb by mass, further preferably less than 410 ppb by mass, and particularly preferably less than 150 ppb by mass. The hexyl iodide concentration in the second acetic acid stream is, for example, 0.2 to 10,000 ppb by mass, normally 1 to 1,000 ppb by mass, and often 2 to 100 ppb by mass (e.g., 3 to 50 ppb by mass, and particularly 5 to 40 ppb by mass).

To the second acetic acid stream flowing through the line 34, potassium hydroxide can be fed or added through the line 56 (potassium hydroxide introduction line). The potassium hydroxide can be fed or added, for example, as a solution such as an aqueous solution. Hydrogen iodide in the second acetic acid stream can be decreased by the feed or addition of potassium hydroxide to the second acetic acid stream. Specifically, the hydrogen iodide reacts with the potassium hydroxide to form potassium iodide and water. This can reduce the corrosion of an apparatus such as a distillation column ascribable to hydrogen iodide.

The distillation column 6 is a unit for performing the third distillation step and serves as the so-called higher boiling point component removal column in the present embodiment. The third distillation step is a step for further purifying acetic acid by the purification treatment of the second acetic acid stream continuously introduced to the distillation column 6. At the distillation column 6, as defined by the present invention, it is preferable to obtain purified acetic acid by distilling the second acetic acid stream fed via the line 34 at a column bottom temperature of less than 175° C. Further, as defined by the present invention, it is preferred that the material of the line 34 and the material of the distillation column 6 (at least the material of the portions in contact with the liquids and gases) be a nickel base alloy or zirconium. By using such a material, corrosion of the pipes and the inner portions of the distillation column by hydrogen iodide and acetic acid can be suppressed, and elution of corroded metal ions can also be suppressed.

The charging mixture of the distillation column 6 includes at least a part (line 34) of the second acetic acid stream, to which a stream other than the second acetic acid stream [e.g., a recycle stream from a downstream step (e.g., a recycle stream of the bottom fraction from the column bottom of the product column, described below)] may be added. In the present invention, it is preferable to set the metal ion concentrations in the charging mixture of the distillation column 6 to be less than 10,000 ppb by mass of iron ions, less than 5,000 ppb by mass of chromium ions, less than 3,000 ppb by mass of nickel ions, and less than 2,000 ppb by mass of molybdenum ions. By employing the above-described specific material for the material of the distillation column 6, setting the column bottom temperature to less than 175° C., and controlling the metal ion concentrations in the charging mixture to the distillation column 6 within the above-described ranges, the corroded metal concentrations in the purified acetic acid obtained in this step can be remarkably reduced, the metal concentrations in the acetic acid fed to the subsequent adsorptive removal step can also be reduced, and the life of the silver-substituted ion exchange resin (IER) can be substantially improved. It is preferred that the iron ion concentration in the charging mixture of the distillation column 6 be less than 9000 ppb by mass, more preferably less than 5,000 ppb by mass, even more preferably less than 3,000 ppb by mass, particularly preferably less than 1,500 ppb by mass, and especially preferably less than 800 ppb by mass (e.g., less than 400 ppb by mass). It is preferred that the chromium ion concentration in the charging mixture be less than 4,000 ppb by mass, more preferably less than 2,500 ppb by mass, even more preferably less than 1,500 ppb by mass, particularly preferably less than 750 ppb by mass, and especially preferably less than 400 ppb by mass (e.g., less than 200 ppb by mass). It is preferred that the nickel ion concentration in the charging mixture be less than 2,500 ppb by mass, more preferably less than 2,000 ppb by mass, even more preferably less than 1,000 ppb by mass, particularly preferably less than 500 ppb by mass, and especially preferably less than 250 ppb by mass (e.g., less than 150 ppb by mass). It is preferred that the molybdenum ion concentration in the charging mixture be less than 1,700 ppb by mass, more preferably less than 1,200 ppb by mass, even more preferably less than 700 ppb by mass, particularly preferably less than 350 ppb by mass, and especially preferably less than 170 ppb by mass. Further, the zinc ion concentration in the charging mixture is, for example, less than 1,000 ppb by mass, preferably less than 800 ppb by mass, more preferably less than 650 ppb by mass, even more preferably less than 500 ppb by mass, particularly preferably less than 410 ppb by mass, and especially preferably less than 200 ppb by mass. The hexyl iodide concentration in the charging mixture is, for example, 0.2 to 10,000 ppb by mass, normally 1 to 1,000 ppb by mass, and often 2 to 100 ppb by mass (e.g., 3 to 50 ppb by mass, and particularly 5 to 40 ppb by mass). Further, the acetic acid concentration in the charging mixture of the distillation column 6 is, for example, 90% by mass or more (e.g., 95% by mass or more), more preferably 97% by mass or more, even more preferably 98% by mass or more, and particularly preferably 99% by mass or more. In addition, the charging mixture of the distillation column 6 may contain at least one compound selected from the group consisting of an acetate salt, acetic anhydride, and propionic acid.

The distillation column 6 consists of, for example, a distillation column such as a plate column or a packed column. In the case of adopting a plate column as the distillation column 6, the theoretical number of plates thereof is, for example, 5 to 50, and the reflux ratio is, for example, 0.2 to 3000 according to the theoretical number of plates.

In the inside of the distillation column 6 that is at the third distillation step, it is preferred that the column top pressure and the column bottom pressure be set in accordance with the column bottom liquid composition such that the column bottom temperature is less than 175° C. The column top pressure is, for example, 0.005 to 0.24 MPaG, preferably 0.01 to 0.22 MPaG, more preferably 0.02 to 0.20 MPaG, and particularly preferably 0.04 to 0.19 MPaG. The column bottom pressure is higher than the column top pressure, and is, for example, 0.01 MPaG or more and less than 0.255 MPaG, preferably 0.02 to 0.24 MPaG, more preferably 0.03 to 0.23 MPaG, and particularly preferably 0.05 to 0.21 MPaG. In the inside of the distillation column 6 that is at the third distillation step, the column top temperature is, for example, a temperature higher than the boiling point of water and lower than the boiling point of acetic acid at the set column top pressure, and is set to 50° C. or more and less than 170° C. The column top temperature is, for example, 168° C. or less, preferably 167° C. or less, more preferably less than 167° C., even more preferably less than 165° C., still even more preferably less than 163° C., particularly preferably less than 161° C., and especially preferably less than 160° C. The lower limit of the column top temperature of the distillation column is, for example, 50° C., preferably 90° C., more preferably 100° C., and even more preferably 110° C. The column bottom temperature is, for example, a temperature higher than the boiling point of acetic acid at the set column bottom pressure, and is set to 70° C. or more and less than 175° C. The column bottom temperature is preferably 173° C. or less (e.g., less than 173° C.), more preferably 172° C. or less (e.g., 170° C. or less), even more preferably 168° C. or less (e.g., 165° C. or less), particularly preferably 165° C. or less (e.g., 164° C. or less), and especially preferably 163° C. or less (e.g., 162° C. or less). Further, the lower limit of the column bottom temperature is, for example, 120° C., preferably 125° C., more preferably 130° C., and more preferably 135° C. Setting the column bottom temperature of the higher boiling point component removal column to less than 175° C. and the column top temperature to within the above range enables corrosion of the inner portions the distillation column due to hydrogen iodide or acetic acid to be suppressed more, and elution of the corroded metal ions to be suppressed more.

A vapor as an overhead stream is continuously withdrawn to the line 38 from the column top of the distillation column 6. A bottom fraction is continuously withdrawn to the line 39 from the column bottom of the distillation column 6. 6b denotes a reboiler. A side stream (liquid or gas) is continuously withdrawn to the line 46 from the height position between the column top and the column bottom of the distillation column 6. The connection position of the line 46 to the distillation column 6 may be, as shown in the drawing, higher than the connection position of the line 34 to the distillation column 6 in the height direction of the distillation column 6, but may be lower than the connection position of the line 34 to the distillation column 6 or may be the same as the connection position of the line 34 to the distillation column 6.

The vapor withdrawn from the column top of the distillation column 6 contains a larger amount of components having a lower boiling point (lower boiling point components) than that of acetic acid as compared with the bottom fraction from the distillation column 6 and contains, in addition to acetic acid, for example, methyl iodide, hydrogen iodide, water, methyl acetate, dimethyl ether, methanol, and formic acid. Such a vapor is continuously introduced to the condenser 6a through the line 38.

The condenser 6a separates the vapor from the distillation column 6 into a condensate portion and a gaseous portion by cooling and partial condensation. The condensate portion contains, in addition to acetic acid, for example, methyl iodide, hydrogen iodide, water, methyl acetate, dimethyl ether, methanol, and formic acid. At least a portion of the condensate portion is continuously refluxed to the distillation column 6 from the condenser 6a through the line 40. A portion (distillate) of the condensate portion may be recycled to the first acetic acid stream in the line 27 before introduction to the distillation column 5 from the condenser 6a through the lines 40, 41, and 42. Together with this or instead of this, a portion (distillate) of the condensate portion may be recycled to the vapor stream in the line 21 before introduction to the distillation column 3 from the condenser 6a through the lines 40, 41, and 43. Also, a portion (distillate) of the condensate portion may be recycled to the reaction vessel 1 from the condenser 6a through the lines 40, 44, and 23. Furthermore, as mentioned above, a portion of the distillate from the condenser 6a may be fed to the scrubber system 8 and used as an absorbing liquid in this system. In the scrubber system 8, a gaseous portion after absorption of a useful portion is discharged to the outside of the apparatus. Then, a liquid portion containing the useful components is introduced or recycled to the reaction vessel 1 from the scrubber system 8 through the recycle lines 48 and 23 and reused. In addition, a portion of the distillate from the condenser 6a may be led to various pumps (not shown) operated in the apparatus, through lines (not shown) and used as sealing solutions in these pumps. In addition, a portion of the distillate from the condenser 6a may be steadily withdrawn to the outside of the apparatus through a withdrawal line attached to the line 40, or may be non-steadily withdrawn to the outside of the apparatus when needed. In the case where a portion (distillate) of the condensate portion is removed from the distillation treatment system in the distillation column 6, the amount of the distillate (ratio of the distillate) is, for example, 0.01 to 30% by mass, preferably 0.1 to 10% by mass, more preferably 0.3 to 5% by mass, more preferably 0.5 to 3% by mass, of the condensate generated in the condenser 6a. On the other hand, the gaseous portion generated in the condenser 6a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 6a through the lines 45 and 15.

The bottom fraction withdrawn from the column bottom of the distillation column 6 via the line 39 contains a larger amount of components having a higher boiling point (higher boiling point components) than that of acetic acid as compared with the overhead stream from the distillation column 6, and contains, for example, acetate salts, acetic anhydride, propionic acid, and the like. Examples of the acetate salts include potassium acetate formed when an alkali, such as potassium hydroxide, is fed to the line 34 or the like. Another example of the acetate salt is a metal acetate formed by acetic acid and a corroded metal and the like, such as a metal formed at and released from the inside wall of a member constituting this acetic acid production apparatus. The bottom fraction withdrawn from the column bottom of the distillation column 6 via the line 39 further contains the corroded metals and the like and compounds of the corroded metals and the like and the iodine derived from corrosive iodine. In the present embodiment, such a bottom fraction is discharged outside the acetic acid production apparatus.

In the present invention, from the perspective of suppressing corrosion of the distillation column, it is more preferred that the concentrations of the acetate salts, acetic anhydride, and propionic acid in the column bottom liquid of the distillation column 6 each be lower. The acetate salt concentration in the column bottom liquid of the distillation column 6 is, for example, 1 ppm by mass to 34% by mass, preferably 100 ppm by mass to 25% by mass, and more preferably 0.1 ppm by mass to 20% by mass (e.g., 1 to 15% by mass). The acetic anhydride concentration in the column bottom liquid of the distillation column 6 is, for example, 1 ppm by mass to 91% by mass (e.g., 1 ppm by mass to 90% by mass), preferably 10 ppm by mass to 74% by mass, more preferably 100 ppm by mass to 44% by mass, even more preferably 0.1 to 20% by mass, and particularly preferably 0.2 to 10% by mass (e.g., 0.5 to 5% by mass). The propionic acid concentration in the column bottom liquid of the distillation column 6 is, for example, 100 ppm by mass to 91% by mass (e.g., 1 ppm by mass to 90% by mass), preferably 0.1 to 75% by mass, more preferably 0.3 to 55% by mass, even more preferably 0.5 to 29% by mass, and particularly preferably 1 to 15% by mass. The acetate salt concentration in the column bottom liquid of the distillation column 6 can be reduced by, for example, reducing the added amount of alkali used for neutralization of the hydrogen iodide, or making corrosion inside the distillation column more difficult to occur. Further, the acetic anhydride concentration in the column bottom liquid of the distillation column 6 can also be reduced by, for example, adding water to the pipes or apparatus positioned upstream of the distillation column 6 or to the distillation column 6 to hydrolyze the acetic anhydride. The concentration of propionic acid in the column bottom liquid of the distillation column 6 can be reduced by, for example, changing the reaction conditions to reduce the amount of propionic acid produced as by-products in the reaction vessel, or during the recycling of a part of the process liquid to the reaction system, separating and removing acetaldehyde, which is a cause of propionic acid by-product production, from the process liquid and then recycling the resultant process liquid to the reaction system, or providing a distillation column or an evaporator (propionic acid removal column) for separating and removing propionic acid upstream of the distillation column 6.

The side stream continuously withdrawn to the line 46 from the distillation column 6 is continuously introduced as a third acetic acid stream to the next ion exchange resin column 7. This third acetic acid stream is more enriched with acetic acid than the second acetic acid stream continuously introduced to the distillation column 6. Specifically, the acetic acid concentration of the third acetic acid stream is higher than the acetic acid concentration of the second acetic acid stream. The acetic acid concentration of the third acetic acid stream is, for example, 99.8 to 99.999% by mass as long as being higher than the acetic acid concentration of the second acetic acid stream. The hexyl iodide concentration in the third acetic acid stream is, for example, 0.2 to 10,000 ppb by mass, normally 1 to 1,000 ppb by mass, and often 2 to 100 ppb by mass (e.g., 3 to 50 ppb by mass, and particularly 5 to 40 ppb by mass). In the present embodiment, the withdrawal position of the side stream from the distillation column 6 is higher than the introduction position of the second acetic acid stream to the distillation column 6 in the height direction of the distillation column 6. In another embodiment, the withdrawal position of the side stream from the distillation column 6 is the same as or lower than the introduction position of the second acetic acid stream to the distillation column 6 in the height direction of the distillation column 6. A simple distillator (evaporator) may be used in place of the distillation column 6. Also, the distillation column 6 can be omitted as long as the removal of impurities in the distillation column 5 is adequately performed.

The ion exchange resin column 7 is a purification unit for performing the adsorptive removal step. This adsorptive removal step is a step for further purifying acetic acid by the adsorptive removal of, mainly, alkyl iodides (e.g., ethyl iodide, propyl iodide, butyl iodide, hexyl iodide, and decyl iodide) contained in a very small amount in the third acetic acid stream continuously introduced to the ion exchange resin column 7. In the ion exchange resin column 7, an ion exchange resin having the ability to adsorb alkyl iodides is packed in the column to establish an ion exchange resin bed. Examples of such an ion exchange resin include cation exchange resins in which a portion of leaving protons in an exchange group such as a sulfonic acid group, a carboxyl group, or a phosphonic acid group is substituted by a metal such as silver or copper. In the adsorptive removal step, for example, the third acetic acid stream (liquid) flows through the inside of the ion exchange resin column 7 packed with such an ion exchange resin, and in the course of this flow, impurities such as the alkyl iodides in the third acetic acid stream are adsorbed to the ion exchange resin and removed from the third acetic acid stream. In the ion exchange resin column 7 in the adsorptive removal step, the internal temperature is, for example, 18 to 100° C., and the rate of the acetic acid stream [the throughput of acetic acid per $m^3$ resin volume ($m^3$/h)] is, for example, 3 to 15 $m^3/h \cdot m^3$ (resin volume).

A fourth acetic acid stream is continuously led to the line 47 from the lower end of the ion exchange resin column 7. The acetic acid concentration of the fourth acetic acid stream is higher than the acetic acid concentration of the third acetic acid stream. Specifically, the fourth acetic acid stream is more enriched with acetic acid than the third acetic acid stream continuously introduced to the ion exchange resin column 7. The acetic acid concentration of the fourth acetic acid stream is, for example, 99.9 to 99.999% by mass or not less than this range as long as being higher than the acetic acid concentration of the third acetic acid stream. The hexyl iodide concentration in the fourth acetic acid stream is normally not more than 1 ppb by mass, but may be, for example, 0 to 30 ppb by mass, and particularly 0.01 to 10 ppb by mass (e.g., 0.1 to 5 ppb by mass). In this production method, this fourth acetic acid stream can be retained in a product tank (not shown).

In this acetic acid production apparatus, a so-called product column or finishing column which is a distillation column may be disposed as a purification unit for further purifying the fourth acetic acid stream from the ion exchange resin column 7. It is preferable to obtain purified acetic acid by distilling the fourth acetic acid stream supplied via the line 47 under conditions of a column bottom temperature of less than 175° C. in the product column. In the case where such a product column is disposed, the product column consists of, for example, a distillation column such as a plate column or a packed column. In the case of adopting a plate column as the product column, the theoretical number of plates thereof is, for example, 5 to 50, and the reflux ratio is, for example, 0.5 to 3000 according to the theoretical number of plates. In the inside of the product column that is at the purification step, it is preferred that the column top pressure and the column bottom pressure be set in accordance with the column bottom liquid composition such that the column bottom temperature is less than 175° C. The column top pressure is, for example, 0.005 to 0.24 MPaG, preferably 0.01 to 0.22 MPaG, more preferably 0.02 to 0.20 MPaG, and particularly preferably 0.04 to 0.19 MPaG. The column bottom pressure is higher than the column top pressure, and is, for example, 0.01 MPaG or more and less than 0.255 MPaG, preferably 0.02 to 0.24 MPaG, more preferably 0.03 to 0.23 MPaG, and particularly preferably 0.05 to 0.21 MPaG. In the inside of the product column that is at the purification step, the column top temperature is, for example, a temperature higher than the boiling point of water and lower than the boiling point of acetic acid at the set column top pressure, and is set to 50° C. or more and less than 170° C. The column top temperature is, for example, 168° C. or less, preferably 167° C. or less, more preferably less than 167° C., even more preferably less than 165° C., still even more preferably less than 163° C., particularly preferably less than 161° C., and especially preferably less than 160° C. The lower limit of the column top temperature of the distillation column is, for example, 50° C., preferably 90° C., more preferably 100° C., and even more preferably 110° C. The column bottom temperature is, for example, a temperature higher than the boiling point of acetic acid at the set column bottom pressure, and is set to 70° C. or more and less than 175° C. (preferably 173° C. or less (e.g., less than 173° C.), more preferably 172° C. or less (e.g., 170° C. or less), even more preferably 168° C. or less (e.g., 165° C. or less), particularly preferably 165° C. or less (e.g., 164° C. or less), and especially preferably 163° C. or less (e.g., 162° C. or less)). Further, the lower limit of the column bottom temperature is, for example, 120° C., preferably 125° C., more preferably 130° C., and more preferably 135° C. A simple distillator (evaporator) may be used in place of the product column or the finishing column.

In the case of disposing the product column, the whole or a portion of the fourth acetic acid stream (liquid) from the ion exchange resin column 7 is continuously introduced to the product column. A vapor as an overhead stream containing a very small amount of lower boiling point components (e.g., methyl iodide, water, methyl acetate, dimethyl ether, crotonaldehyde, acetaldehyde, and formic acid) is continuously withdrawn from the column top of such a product column. This vapor is separated into a condensate portion and a gaseous portion in a predetermined condenser. A portion of the condensate portion is continuously refluxed to the product column, and another portion of the condensate portion may be recycled to the reaction vessel 1 or discarded to the outside of the system, or both. The gaseous portion is fed to the scrubber system 8. A bottom fraction containing a very small amount of higher boiling point components is continuously withdrawn from the column bottom of the product column. This bottom fraction is recycled to, for example, the second acetic acid stream in the line 34 before introduction to the distillation column 6. A side stream (liquid) is continuously withdrawn as a fifth acetic acid stream from the height position between the column top and the column bottom of the product column. The withdrawal position of the side stream from the product column is lower than, for example, the introduction position of the fourth acetic acid stream to the product column in the height direction of the product column. The fifth acetic acid stream is more enriched with acetic acid than the fourth acetic acid stream continuously introduced to the product column. Specifically, the acetic acid concentration of the fifth acetic acid stream is higher than the acetic acid concentration of the fourth acetic acid stream. The acetic acid concentration of the fifth acetic acid stream is, for example, 99.9 to 99.999% by mass or not less than this range as long as being higher than the acetic acid concentration of the fourth acetic acid stream. The hexyl iodide concentration in the fifth acetic acid stream is normally not more than 1 ppb by mass, but may be, for example, 0 to 30 ppb by mass, and particularly 0.01 to 10 ppb by mass (e.g., 0.1 to 5 ppb by mass). This fifth acetic acid stream is retained in, for example, a product tank (not shown). The ion exchange resin column 7 may be placed downstream of the product column instead of (or in addition to) its placement downstream of the distillation column 6 to treat the acetic acid stream from the product column.

In the case where the product column is placed upstream of the ion exchange resin column 7, as defined by the present invention, it is preferable to obtain purified acetic acid by distilling the acetic acid stream fed at a column bottom temperature of less than 175° C. Further, as defined by the present invention, it is preferred that the material of the pipes and the material of the product column (at least the material of the portions in contact with the liquids and gases) be a nickel base alloy or zirconium. By using such a material, corrosion of the pipes and the inner portions of the distillation column by hydrogen iodide and acetic acid can be suppressed, and elution of corroded metal ions can also be suppressed.

In the present invention, from the perspective of suppressing corrosion of the distillation column, it is more preferred that the concentrations of the acetate salts, acetic anhydride, and propionic acid in the column bottom liquid of the product column each be lower. The acetate salt concentration in the column bottom liquid of the product column is, for example, 0.1 ppb by mass to 1% by mass, preferably 1 ppb by mass to 0.1% by mass, and more preferably 10 ppb by mass to 0.01% by mass (e.g., 100 ppb by mass to 0.001% by mass). The acetic anhydride concentration in the column bottom liquid of the product column is, for example, 0.1 ppm by mass to 60% by mass, preferably 1 ppm by mass to 10% by mass, more preferably 10 ppm by mass to 2% by mass (e.g., 50 ppm by mass to 0.5% by mass), or may even be 0.2 to 10% by mass (e.g., 0.5 to 5% by mass). The propionic acid concentration in the column bottom liquid of the product column is, for example, 1 ppm by mass to 10% by mass, preferably 10 ppm by mass to 5% by mass, and more preferably 50 ppm by mass to 1% by mass (e.g., 100 ppm by mass to 0.1% by mass). The acetate salt concentration in the column bottom liquid of the product column can be reduced by, for example, reducing the added amount of alkali used for neutralization of the hydrogen iodide, or making corrosion inside the distillation column more difficult to occur. Further, the acetic anhydride concentration in the column bottom liquid of the product column can also be reduced by, for example, adding water to the pipes or apparatus positioned upstream of the product column or to the product column to hydrolyze the acetic anhydride. The concentration of propionic acid in the column bottom liquid of the product column can be reduced by, for example, changing the reaction conditions to reduce the amount of propionic acid produced as by-products in the reaction vessel, or during the recycling of a part of the process liquid to the reaction system, separating and removing acetaldehyde, which is a cause of propionic acid by-product production, from the process liquid and then recycling the resultant process liquid to the reaction system, or providing a distillation column or an evaporator (propionic acid removal column) for separating and removing propionic acid upstream of the product column.

The charging mixture of the product column includes at least a part of the acetic acid stream to be distilled, to which a stream other than that acetic acid stream may be added. In the case where the product column is placed upstream of the ion exchange resin column 7, in the present invention, it is preferable to set the metal ion concentrations in the charging mixture of the product column to be less than 10,000 ppb by mass of iron ions, less than 5,000 ppb by mass of chromium ions, less than 3,000 ppb by mass of nickel ions, and less than 2,000 ppb by mass of molybdenum ions. By employing the above-described specific material for the material of the product column, setting the column bottom temperature to less than 175° C., and controlling the metal ion concentrations in the charging mixture to the product column within the above-described ranges, the corroded metal concentrations in the purified acetic acid obtained in this step can be remarkably reduced, the metal concentrations in the acetic acid fed to the subsequent adsorptive removal step can also be reduced, and the life of the silver-substituted ion exchange resin (IER) can be substantially improved. It is preferred that the iron ion concentration in the charging mixture of the product column be less than 9,000 ppb by mass, more preferably less than 5,000 ppb by mass, even more preferably less than 3,000 ppb by mass, particularly preferably less than 1,500 ppb by mass, and especially preferably less than 800 ppb by mass (e.g., less than 400 ppb by mass). It is preferred that the chromium ion concentration in the charging mixture be less than 4,000 ppb by mass, more preferably less than 2,500 ppb by mass, even more preferably less than 1,500 ppb by mass, particularly preferably less than 750 ppb by mass, and especially preferably less than 400 ppb by mass (e.g., less than 200 ppb by mass). It is preferred that the nickel ion concentration in the charging mixture be less than 2,500 ppb by mass, more preferably less than 2,000 ppb by mass, even more preferably less than 1,000 ppb by mass, particularly preferably less than 500 ppb by mass, and especially preferably less than 250 ppb by mass (e.g., less than 150 ppb by mass). It is preferred that the molybdenum ion concentration in the charging mixture be less than 1,700 ppb by mass, more preferably less than 1,200 ppb by mass, even more preferably less than 700 ppb by mass, particularly preferably less than 350 ppb by mass, and especially preferably less than 170 ppb by mass. Further, the zinc ion concentration in the charging mixture is, for example, less than 1,000 ppb by mass, preferably less than 800 ppb by mass, more preferably less than 650 ppb by mass, even more preferably less than 500 ppb by mass, particularly preferably less than 410 ppb by mass, and especially preferably less than 200 ppb by mass. The hexyl iodide concentration in the charging mixture is, for example, 0.2 to 10,000 ppb by mass, normally 1 to 1,000 ppb by mass, and often 2 to 100 ppb by mass (e.g., 3 to 50 ppb by mass, and particularly 5 to 40 ppb by mass). Further, the acetic acid concentration in the charging mixture of the product column is, for example, 90% by mass or more (e.g., 95% by mass or more), more preferably 97% by mass or more, even more preferably 98% by mass or more, and particularly preferably 99% by mass or more. In addition, the charging mixture of the product column may contain at least one compound selected from the group consisting of an acetate salt, acetic anhydride, and propionic acid.

In the above embodiment, for example, of the distillation column 5 and the distillation column 6, the column bottom temperature of the distillation column 5 may be set to less than 175° C. (e.g., 173° C. or less), and the column bottom temperature of the distillation column 6 may be set to less than 175° C. (e.g., 173° C. or less), or the column bottom temperature of the distillation column 5 and the distillation column 6 may be set to less than 175° C. (e.g., 173° C. or less). Further, when the product column is placed upstream of the ion exchange resin column 7, in addition to the above examples, among the distillation column 5, the distillation column 6, and the product column, for example, the column bottom temperature of the product column may be set to less than 175° C. (e.g., 173° C. or less), the column bottom temperature of the distillation column 5 and the product column may be set to less than 175° C. (e.g., 173° C. or less), the column bottom temperature of the distillation column 6 and the product column may be set to less than 175° C. (e.g., 173° C. or less), or the column bottom temperature of all three of the distillation columns, namely, the distillation column 5, the distillation column 6, and the product column, may be set to less than 175° C. (e.g., 173° C. or less). Each column bottom temperature is preferably less than 173° C., more preferably 172° C. or less (e.g., 170° C. or less), even more preferably 168° C. or less (e.g. 165° C. or less), particularly preferably 165° C. or less (e.g., 164° C. or less), and especially preferably 163° C. or less (e.g., 162° C. or less). As described above, the distillation column 6 and the product column (particularly the latter) do not always need to be provided.

EXAMPLES

Hereinafter, the present invention will be described in more detail with reference to Examples. However, the present invention is not intended to be limited by these Examples. The units %, ppm, and ppb are each expressed in terms of mass. A water concentration was measured by the Karl Fischer water determination method, metal ion concentrations were measured by ICP analysis (or atomic adsorption analysis), and concentrations of other components were measured by gas chromatography.

Comparative Example 1

In a continuous reaction process for producing acetic acid, methanol and carbon monoxide were continuously reacted in a carbonylation reaction vessel, the reaction mixture from the reaction vessel was continuously fed into a flasher, a volatile component containing at least acetic acid, methyl acetate, methyl iodide, water, and hydrogen iodide produced by flash distillation was fed to a first distillation column (lower boiling point component removal column), a first lower boiling point component was separated as an overhead, and a stream containing a large amount of components with a higher boiling point than acetic acid was separated as a bottom fraction from the column bottom. The overhead fraction (first lower boiling point component) was directly recycled to the reaction vessel, and the bottom fraction from the column bottom was mixed with the bottom fraction of the flasher and recycled to the reaction vessel. Then a first liquid stream portion was withdrawn from a side stream of the first distillation column, passed through a pipe made of a stainless steel material (SUS316: not more than 2% of Mn, 10 to 14% of Ni, 16 to 18% of Cr, 2 to 3% of Mo, and not less than 50% of Fe), and continuously fed into a second distillation column (dehydration column) (actual number of plates: 50, plate spacing between a feeding plate and a column top vapor withdrawal plate: 15 plates in terms of actual plates) made of the SUS316 material. The composition of the first liquid stream portion was 2% of methyl iodide, 2% of methyl acetate, 1% of water, 9,100 ppb of iron ions, 4,000 ppb of chromium ions, 2,500 ppb of nickel ions, 1,700 ppb of molybdenum ions, 410 ppb of zinc ions, 51 ppb of hexyl iodide, and acetic acid as a balance (90% by mass or more, including a very small amount of impurities such as acetate salts, acetic anhydride, and propionic acid). In the dehydration column, distillation was carried out under conditions of a column top temperature of 165° C. and a column bottom temperature of 175° C., a water-containing second lower boiling point component was concentrated at the column top, and a second liquid stream portion (purified acetic acid) was obtained as a bottom fraction. The distillate from the column top was recycled to the reaction vessel. Based on an amount fed into the dehydration column of 1, the amount of the bottom fraction was 0.7 and the amount of the distillate from the column top was 0.3. The composition of the bottom fraction was 500 ppm of water, 21,000 ppb of iron ions, 8,300 ppb of chromium ions, 5,200 ppb of nickel ions, 2,800 ppb of molybdenum ions, 590 ppb of zinc ions, 50 ppb of hexyl iodide, less than 50 ppm of acetate salt, 110 ppm of acetic anhydride, 120 ppm of propionic acid, and acetic acid as a balance (including a very small amount of impurities). The bottom fraction was cooled to 40 to 50° C., and then passed through a two meter long silver-substituted ion exchange resin (IER) column to adsorb and remove the hexyl iodide in the acetic acid. The flow rate of the bottom fraction [the throughput of bottom fraction per $m^3$ resin volume ($m^3$/h)] was 3.8 $m^3$/h·$m^3$ (resin volume). After the silver-substituted ion exchange resin treatment, the silver ion concentration of the product acetic acid was 41 ppb, the iron ion concentration was 100 ppb, the chromium ion concentration was 15 ppb, the nickel ion concentration was 10 ppb, the molybdenum ion concentration was 6 ppb, the zinc ion concentration was 7 ppb, and the hexyl iodide concentration was less than 5 ppb (not more than the limit of detection). The IER resin life (operating time until the hexyl iodide concentration at the resin outlet exceeds 5 ppb) under this operation was 1.2 years. The corrosion rate was, based on a corrosion rate (reduction in thickness) per year of a test piece (SUS 316) calculated in terms of mm, 2.69 mm/Y.

Comparative Example 2

The same experiment as in Comparative Example 1 was conducted except that: the material of the dehydration column was changed to a nickel base alloy [Hastelloy B2 (HB2): 28% of Mo, 69% of Ni, not more than 1% of Cr, not more than 2% of Fe, not more than 1% of Co, and not more than 1% of Mn]; the operating conditions of the dehydration column were set to a column top temperature of 160° C. and a column bottom temperature of 170° C.; and the composition of the charging mixture fed to the dehydration column was 2% of methyl iodide, 2% of methyl acetate, 1% of water, 13,700 ppb of iron ions, 6,000 ppb of chromium ions, 3,800 ppb of nickel ions, 2,600 ppb of molybdenum ions, 620 ppb of zinc ions, 51 ppb of hexyl iodide, and acetic acid as a balance (90% by mass or more, including a very small amount of impurities such as acetate salts, acetic anhydride, and propionic acid).

The composition of the bottom fraction of the dehydration column was 490 ppm of water, 19,700 ppb of iron ions, 8,700 ppb of chromium ions, 7,000 ppb of nickel ions, 4,300 ppb of molybdenum ions, 890 ppb of zinc ions, 51 ppb of hexyl iodide, less than 50 ppm of acetate salt, 110 ppm of acetic anhydride, 120 ppm of propionic acid, and acetic acid as a balance (including a very small amount of impurities). Further, after the silver-substituted ion exchange resin treatment, the silver ion concentration of the product acetic acid was 30 ppb, the iron ion concentration was 80 ppb, the chromium ion concentration was 16 ppb, the nickel ion concentration was 15 ppb, the molybdenum ion concentration was 9 ppb, the zinc ion concentration was 9 ppb, and the hexyl iodide concentration was less than 5 ppb (not more than the limit of detection). The IER resin life under this operation was 1.1 years, and the corrosion rate was 0.39 mm/Y.

Comparative Example 3

The same experiment as in Comparative Example 1 was conducted except that the operating conditions of the dehydration column were set to a column top temperature of 160° C. and a column bottom temperature of 170° C.

The composition of the bottom fraction of the dehydration column was 490 ppm of water, 19,800 ppb of iron ions, 7,900 ppb of chromium ions, 4,900 ppb of nickel ions, 2,700 ppb of molybdenum ions, 590 ppb of zinc ions, 49 ppb of hexyl iodide, less than 50 ppm of acetate salt, 110 ppm of acetic anhydride, 120 ppm of propionic acid, and acetic acid as a balance (including a very small amount of impurities). Further, after the silver-substituted ion exchange resin treatment, the silver ion concentration of the product acetic acid was 34 ppb, the iron ion concentration was 85 ppb, the chromium ion concentration was 14 ppb, the nickel ion concentration was 9 ppb, the molybdenum ion concentration was 7 ppb, the zinc ion concentration was 5 ppb, and the hexyl iodide concentration was less than 5 ppb (not more than the limit of detection). The IER resin life under this operation was 1.2 years, and the corrosion rate was 2.28 mm/Y.

Comparative Example 4

The same experiment as in Comparative Example 1 was conducted except that the operating conditions of the dehydration column were set to a column top temperature of 155° C. and a column bottom temperature of 165° C.

The composition of the bottom fraction of the dehydration column was 500 ppm of water, 16,000 ppb of iron ions, 6,700 ppb of chromium ions, 4,200 ppb of nickel ions, 2,600 ppb of molybdenum ions, 590 ppb of zinc ions, 45 ppb of hexyl iodide, less than 50 ppm of acetate salt, 110 ppm of acetic anhydride, 120 ppm of propionic acid, and acetic acid as a balance (including a very small amount of impurities). Further, after the silver-substituted ion exchange resin treatment, the silver ion concentration of the product acetic acid was 29 ppb, the iron ion concentration was 81 ppb, the chromium ion concentration was 13 ppb, the nickel ion concentration was 9 ppb, the molybdenum ion concentration was 8 ppb, the zinc ion concentration was 5 ppb, and the hexyl iodide concentration was less than 5 ppb (not more than the limit of detection). The IER resin life under this operation was 1.4 years, and the corrosion rate was 1.00 mm/Y.

Comparative Example 5

The same experiment as in Comparative Example 1 was conducted except that the material of the dehydration column was changed to a nickel base alloy [Hastelloy B2 (HB2)].

The composition of the bottom fraction of the dehydration column was 510 ppm of water, 13,200 ppb of iron ions, 5,800 ppb of chromium ions, 6,900 ppb of nickel ions, 3,800 ppb of molybdenum ions, 590 ppb of zinc ions, 43 ppb of hexyl iodide, less than 50 ppm of acetate salt, 110 ppm of acetic anhydride, 120 ppm of propionic acid, and acetic acid as a balance (including a very small amount of impurities). Further, after the silver-substituted ion exchange resin treatment, the silver ion concentration of the product acetic acid was 30 ppb, the iron ion concentration was 80 ppb, the chromium ion concentration was 16 ppb, the nickel ion concentration was 15 ppb, the molybdenum ion concentration was 9 ppb, the zinc ion concentration was 9 ppb, and the hexyl iodide concentration was less than 5 ppb (not more than the limit of detection). The IER resin life under this operation was 1.3 years, and the corrosion rate was 0.82 mm/Y.

Example 1

The same experiment as in Comparative Example 1 was conducted except that: the material of the dehydration column was changed to a nickel base alloy [Hastelloy B2 (HB2)]; and the operating conditions of the dehydration column were set to a column top temperature of 160° C. and a column bottom temperature of 170° C.

The composition of the bottom fraction of the dehydration column was 490 ppm of water, 13,200 ppb of iron ions, 5,800 ppb of chromium ions, 5,200 ppb of nickel ions, 3,100 ppb of molybdenum ions, 590 ppb of zinc ions, 52 ppb of hexyl iodide, less than 50 ppm of acetate salt, 110 ppm of acetic anhydride, 120 ppm of propionic acid, and acetic acid as a balance (including a very small amount of impurities). Further, after the silver-substituted ion exchange resin treatment, the silver ion concentration of the product acetic acid was 18 ppb, the iron ion concentration was 25 ppb, the chromium ion concentration was 9 ppb, the nickel ion concentration was 8 ppb, the molybdenum ion concentration was 6 ppb, the zinc ion concentration was 7 ppb, and the hexyl iodide concentration was less than 5 ppb (not more than the limit of detection). The IER resin life under this operation was 1.8 years, and the corrosion rate was 0.39 mm/Y.

Example 2

The same experiment as in Example 1 was conducted except that a mixture liquid of 2% of methyl iodide, 2% of methyl acetate, 1% of water, 500 ppb of iron ions, 280 ppb of chromium ions, 190 ppb of nickel ions, 110 ppb of molybdenum ions, 410 ppb of zinc ions, 51 ppb of hexyl iodide, and acetic acid as a balance (90% by mass or more, including a very small amount of impurities such as acetate salts, acetic anhydride, and propionic acid) obtained by passing the first liquid stream portion withdrawn from a side stream of the first distillation column (lower boiling point component removal column) through a pipe made of a nickel base alloy [Hastelloy B2 (HB2)] material was used as the charging mixture fed to the dehydration column.

The composition of the bottom fraction of the dehydration column was 490 ppm of water, 770 ppb of iron ions, 420 ppb of chromium ions, 1,900 ppb of nickel ions, 800 ppb of molybdenum ions, 590 ppb of zinc ions, 50 ppb of hexyl iodide, less than 50 ppm of acetate salt, 110 ppm of acetic anhydride, 120 ppm of propionic acid, and acetic acid as a balance (including a very small amount of impurities). Further, after the silver-substituted ion exchange resin treatment, the silver ion concentration of the product acetic acid was 5 ppb, the iron ion concentration was 6 ppb, the chromium ion concentration was 6 ppb, the nickel ion concentration was 7 ppb, the molybdenum ion concentration was 4 ppb, the zinc ion concentration was 4 ppb, and the hexyl iodide concentration was less than 5 ppb (not more than the limit of detection). The IER resin life under this operation was 6.1 years, and the corrosion rate was 0.39 mm/Y.

Example 3

The same experiment as in Example 1 was conducted except that the material of the dehydration column was changed to a nickel base alloy [Hastelloy C (HC276): 16% of Mo, around 57% of Ni, 16% of Cr, 5% of Fe, not more than 2.5% of Co, and not more than 1% of Mn].

The composition of the bottom fraction of the dehydration column was 520 ppm of water, 13,300 ppb of iron ions, 6,400 ppb of chromium ions, 5,800 ppb of nickel ions, 3,100 ppb of molybdenum ions, 590 ppb of zinc ions, 48 ppb of hexyl iodide, less than 50 ppm of acetate salt, 110 ppm of acetic anhydride, 120 ppm of propionic acid, and acetic acid as a balance (including a very small amount of impurities). Further, after the silver-substituted ion exchange resin treatment, the silver ion concentration of the product acetic acid was 16 ppb, the iron ion concentration was 28 ppb, the chromium ion concentration was 12 ppb, the nickel ion concentration was 13 ppb, the molybdenum ion concentration was 7 ppb, the zinc ion concentration was 4 ppb, and the hexyl iodide concentration was less than 5 ppb (not more than the limit of detection). The IER resin life under this operation was 1.7 years, and the corrosion rate was 0.67 mm/Y.

Example 4

The same experiment as in Example 1 was conducted except that the operating conditions of the dehydration column were set to a column top temperature of 155° C. and a column bottom temperature of 165° C.

The composition of the bottom fraction of the dehydration column was 490 ppm of water, 13,200 ppb of iron ions, 5,800 ppb of chromium ions, 5,200 ppb of nickel ions, 3,100 ppb of molybdenum ions, 590 ppb of zinc ions, 52 ppb of hexyl iodide, less than 50 ppm of acetate salt, 110 ppm of acetic anhydride, 120 ppm of propionic acid, and acetic acid as a balance (including a very small amount of impurities). Further, after the silver-substituted ion exchange resin treatment, the silver ion concentration of the product acetic acid was 13 ppb, the iron ion concentration was 23 ppb, the chromium ion concentration was 8 ppb, the nickel ion concentration was 7 ppb, the molybdenum ion concentration was 5 ppb, the zinc ion concentration was 5 ppb, and the hexyl iodide concentration was less than 5 ppb (not more than the limit of detection). The IER resin life under this operation was 2.0 years, and the corrosion rate was 0.39 mm/Y.

Example 5

The composition of the bottom fraction of the dehydration column was 485 ppm of water, 13,100 ppb of iron ions, 5,800 ppb of chromium ions, 3,900 ppb of nickel ions, 2,600 ppb of molybdenum ions, 590 ppb of zinc ions, 53 ppb of hexyl iodide, less than 50 ppm of acetate salt, 110 ppm of acetic anhydride, 120 ppm of propionic acid, and acetic acid as a balance (including a very small amount of impurities). Further, after the silver-substituted ion exchange resin treatment, the silver ion concentration of the product acetic acid was 12 ppb, the iron ion concentration was 23 ppb, the chromium ion concentration was 9 ppb, the nickel ion concentration was 6 ppb, the molybdenum ion concentration was 5 ppb, the zinc ion concentration was 5 ppb, and the hexyl iodide concentration was less than 5 ppb (not more than the limit of detection). The IER resin life under this operation was 2.1 years, and the corrosion rate was 0.07 mm/Y.

Example 6

The same experiment as in Example 1 was conducted except that the operating conditions of the dehydration column were set to a column top temperature of 163° C. and a column bottom temperature of 173° C.

The composition of the bottom fraction of the dehydration column was 495 ppm of water, 13,200 ppb of iron ions, 5,800 ppb of chromium ions, 5,600 ppb of nickel ions, 3,300 ppb of molybdenum ions, 590 ppb of zinc ions, 51 ppb of hexyl iodide, less than 50 ppm of acetate salt, 110 ppm of acetic anhydride, 120 ppm of propionic acid, and acetic acid as a balance (including a very small amount of impurities). Further, after the silver-substituted ion exchange resin treatment, the silver ion concentration of the product acetic acid was 23 ppb, the iron ion concentration was 40 ppb, the chromium ion concentration was 13 ppb, the nickel ion concentration was 14 ppb, the molybdenum ion concentration was 8 ppb, the zinc ion concentration was 8 ppb, and the hexyl iodide concentration was less than 5 ppb (not more than the limit of detection). The IER resin life under this operation was 1.6 years, and the corrosion rate was 0.49 mm/Y.

Discussion on Results

From Example 1, it is evident that by setting the concentrations of specific metal ions in the charging mixture to the dehydration column to be not more than specific values, and by employing a nickel base alloy having high corrosion resistance for the material of the dehydration column, the amount of metal ions flowing into the dehydration column is reduced, and moreover, in conjunction with performing distillation under conditions of a column bottom temperature of the distillation column of less than 175° C., the elution of corroded metals from the dehydration column is suppressed, which enables the metal ion concentrations in the purified acetic acid obtained from the dehydration column to be greatly reduced. As a result, the amount of metal ions flowing to the subsequent adsorptive removal step of the organic iodine compound could be decreased, the amount of other metal ions exchanged for the silver ions in the silver-substituted ion exchange resin (IER) was reduced, and the IER life was very long, at 1.8 years. Further, the metal ion concentrations in the product acetic acid after the IER treatment decreased, and in conjunction with that the elution of silver ions also decreased. As a result, the quality of the product acetic acid improved. In contrast, in Comparative Example 2, the material of the dehydration column was the same nickel base alloy as in Example 1, but because there was a large amount of metal ions flowing into the dehydration column, there was a large amount of metal ions flowing to the adsorptive removal step, and hence the IER life was short, at 1.1 years. In addition, in Comparative Example 3, the metal ion concentrations in the charging mixture to the dehydration column were the same as those in Example 1, but because the dehydration column material was stainless steel, corroded metals were eluted from the dehydration column, thereby increasing the amount of metal ions flowing to the adsorptive removal step. As a result, the IER life was 1.2 years, which is a low result. It is noted that although the operating temperature in Comparative Example 4 was lower than in Comparative Example 3, because the dehydration column material was stainless steel, the IER life was short, at 1.4 years.

From Examples 1 and 2, even when the materials of the dehydration columns were the same, reducing the concentrations of the corroded metals by controlling the concentrations of those metals in the dehydration column charging mixture also reduced the concentrations of the corroded metals in the purified acetic acid obtained from the dehydration column, and substantially improved the resin life of the silver-substituted ion exchange resin used in the adsorptive removal step. Further, because the corroded metal ion concentrations and the silver ion concentration in the product acetic acid after the IER treatment also decreased, the quality of the acetic acid improved even more. The fact that the metal ion concentrations at the ion exchange resin column outlet were not so much different despite a wide gap between the metal concentrations in the ion exchange resin column charging mixture can be thought as being the result of the ion exchange resin having a sufficiently high exchange capacity and almost all of the metal ions flowing to the ion exchange resin column being removed. In addition, it may be considered that if the experiment is carried out for an even longer duration, in Example 1, which had high metal ion concentrations in the ion exchange resin column charging mixture, the metal ion concentrations at the ion exchange resin column outlet would increase at an earlier stage than in Example 2, which had lower metal ion concentrations.

From Examples 1 and 3, using "HB2", which has an even higher corrosion resistance among nickel base alloys, as the material for the dehydration column enabled elution of the corroded metals to be more suppressed. As a result, the corroded metal ion concentrations in the purified acetic acid obtained from the dehydration column decreased, and the IER resin life and the quality of the product acetic acid improved.

Based on a comparison of Comparative Example 1 and Comparative Example 3, it can be seen that when the dehydration column material is stainless steel, even when the column bottom temperature of the dehydration column is reduced from 175° C. to 170° C., the resin life of the ion exchange resin does not change, staying at 1.2 years. However, based on a comparison between Example 6 and Comparative Example 5, it can be seen that when the column bottom temperature of the dehydration column is reduced from 175° C. to 173° C. when the dehydration column material is the nickel base alloy HB2, the resin life of the ion exchange resin is extended by 0.3 years. In addition, based on a comparison between Comparative Example 5 and Example 1, it can be seen that when the column bottom temperature of the dehydration column is reduced from 175° C. to 170° C. when the dehydration column material is HB2, the resin life of the ion exchange resin is extended by as many as 0.5 years. Further, from Examples 1, 4, 5, and 6, and Comparative Example 5, it can be seen that when the operating temperature of the dehydration column is reduced when the dehydration column material is HB2, the elution amount of corroded metals is reduced and the resin life of the ion exchange resin is improved.

Because the distillation column material does not contain zinc, for all conditions, the increase in zinc ions is only the increase in concentration corresponding to the concentrating rate from the concentrating in the dehydration column, and the absolute amount of the zinc ions in the purified acetic acid was the same as that of the zinc ions fed into the dehydration column.

Summarizing Comparative Examples 1 to 5 and Examples 1 to 6, it is evident that the resin life of an ion exchange resin improves generally in proportion to the decrease in the metal ion concentrations in the ion exchange resin column charging mixture. However, the resin life is not completely proportional to the metal ion concentrations in the ion exchange resin column charging mixture. This is because the amount of organic iodine compounds, such as hexyl iodide, in the ion exchange resin column charging mixture and the amount of silver that is eluted into the acetic acid from the ion exchange resin also affect the resin life. However, it is evident that the metal ion concentrations in the ion exchange resin column charging mixture are one of the main factors in reduction of resin life.

1: reaction vessel
2: evaporator
3, 5, and 6: distillation column
4: decanter
7: ion exchange resin column
8: scrubber system
9: acetaldehyde separation and removal system
16: reaction mixture feed line
17: vapor stream discharge line
18 and 19: residual liquid stream recycle line
54: carbon monoxide-containing gas introduction line
55 and 56: potassium hydroxide introduction line
57: catalyst circulating pump
91: distillation column (first acetaldehyde removal column)
92: extraction column
93: distillation column (second acetaldehyde removal column)
94: distillation column (extractive distillation column)
95: decanter
96: decanter
97: distillation column (acetaldehyde removal column)
98: distillation column (extractive distillation column)
99: decanter
200: chimney tray

The invention claimed is:

1. A method for producing acetic acid, comprising:
a carbonylation reaction step of reacting methanol with carbon monoxide in a reaction vessel in the presence of a catalyst system containing a metal catalyst and methyl iodide, acetic acid, methyl acetate, and water to produce acetic acid;
a separation step of using one or more evaporators and/or distillation columns to separate the reaction mixture obtained in the carbonylation reaction step into a stream containing the metal catalyst, an acetic acid stream rich in acetic acid, and a stream more enriched with a lower boiling point component than the acetic acid stream;
an acetic acid distillation step, optionally included in the separation step, of distilling the acetic acid stream to purify the acetic acid; and
an adsorptive removal step of treating the purified acetic acid stream obtained in the acetic acid distillation step with an ion exchange resin,
wherein the acetic acid distillation step has at least one distillation step (A) of carrying out the purification of the acetic acid stream under conditions of a column bottom temperature of the distillation column of less than 175° C., a nickel base alloy or zirconium is used as a material of the distillation column in the distillation step (A), and as metal ion concentrations in a charging mixture of the distillation column in the distillation step (A), an iron ion concentration is less than 10,000 ppb by mass, a chromium ion concentration is less than 5,000 ppb by mass, a nickel ion concentration is less than 3,000 ppb by mass, and a molybdenum ion concentration is less than 2,000 ppb by mass, and
condition (a) as follows is met and conditions (b) and (c) as follows are optionally met:
(a) adjusting a column bottom liquid of the distillation column in the distillation step (A) to an acetate salt concentration of 0.1 ppm by mass to 1% by mass by reducing an added amount of alkali used for neutralization of hydrogen iodide;
(b) a column bottom liquid of the distillation column in the distillation step (A) has an acetic anhydride concentration of 0.1 ppm by mass to 1% by mass; and
(c) methanol having a zinc ion concentration of less than 10 ppm by mass is used as the raw material methanol in the carbonylation reaction step, and the charging mixture to the distillation column in the distillation step (A) has a zinc ion concentration of less than 1,000 ppb by mass.

2. The method for producing acetic acid according to claim 1, wherein the charging mixture of the distillation column in the distillation step (A) has an acetic acid concentration of 90% by mass or more.

3. The method for producing acetic acid according to claim 1, wherein the charging mixture of the distillation column in the distillation step (A) contains at least one compound selected from the group consisting of an acetate salt, acetic anhydride, and propionic acid.

4. The method for producing acetic acid according to claim 1, wherein a column bottom liquid of the distillation column in the distillation step (A) has a propionic acid concentration of 90% by mass or less.

5. The method for producing acetic acid according to claim 1, wherein the distillation is carried out under conditions of a column bottom pressure of the distillation column in the distillation step (A) of less than 0.255 MPaG.

6. The method for producing acetic acid according to claim 1, wherein the distillation is carried out under conditions of a column bottom pressure of the distillation column in the distillation step (A) of 0.01 MPaG or more and less than 0.255 MPaG.

7. The method for producing acetic acid according to claim 1, wherein the charging mixture of the distillation column in the distillation step (A) has a zinc ion concentration of less than 1,000 ppb by mass.

8. The method for producing acetic acid according to claim 1, wherein a plate spacing between a charging mixture feeding plate and a column top vapor withdrawal plate of the distillation column in the distillation step (A) is not less than one plate in terms of actual plates.

9. The method for producing acetic acid according to claim 1, wherein the material of a charging pipe to the distillation column in the distillation step (A) is a nickel base alloy or zirconium.

10. The method for producing acetic acid according to claim 1, wherein the acetic acid distillation step has at least one distillation step in which the acetic acid concentration in the acetic acid stream to be distilled is 97% by mass or more, and in all such steps the distillation of the acetic acid stream is carried out under conditions of a column bottom temperature of the distillation column of less than 175° C.

11. A method for producing acetic acid, comprising:
a carbonylation reaction step of reacting methanol with carbon monoxide in a reaction vessel in the presence of a catalyst system containing a metal catalyst and methyl iodide, acetic acid, methyl acetate, and water to produce acetic acid;
an evaporation step of separating the reaction mixture obtained in the carbonylation reaction step into a vapor stream and a residual liquid stream in an evaporator;
a lower boiling point component removal step of separating the vapor stream by distillation into an overhead stream rich in a lower boiling point component and a first acetic acid stream rich in acetic acid;
a dehydration step of separating the first acetic acid stream by distillation into an overhead stream rich in water and a second acetic acid stream more enriched with acetic acid than the first acetic acid stream; and
an adsorptive removal step of treating the second acetic acid stream, or an acetic acid stream that has been more enriched with acetic acid by further purification of the second acetic acid stream, with an ion exchange resin,
wherein a nickel base alloy or zirconium is used as a material of a distillation column in the dehydration step, and as metal ion concentrations in a charging mixture of the distillation column in the dehydration step, an iron ion concentration is less than 10,000 ppb by mass, a chromium ion concentration is less than 5,000 ppb by mass, a nickel ion concentration is less than 3,000 ppb by mass, and a molybdenum ion concentration is less than 2,000 ppb by mass, and
the dehydration step is carried out under conditions of a column bottom temperature of the distillation column of less than 175° C., and
condition (a') as follows is met and conditions (b') and (c') as follows are optionally met:
(a') adjusting a column bottom liquid of the distillation column in the dehydration step to an acetate salt concentration of 0.1 ppm by mass to 1% by mass by reducing an added amount of alkali used for neutralization of hydrogen iodide;
(b') a column bottom liquid of the distillation column in the dehydration step has an acetic anhydride concentration of 0.1 ppm by mass to 1% by mass; and
(c') methanol having a zinc ion concentration of less than 10 ppm by mass is used as the raw material methanol in the carbonylation reaction step, and the charging mixture to the distillation column in the distillation step has a zinc ion concentration of less than 1,000 ppb by mass.

12. The method for producing acetic acid according to claim 11, wherein an iron ion concentration in the second acetic acid stream is less than 21,000 ppb by mass.

13. The method for producing acetic acid according to claim 11, wherein as metal ion concentrations in the second acetic acid stream, an iron ion concentration is less than 21,000 ppb by mass, a chromium ion concentration is less than 7,100 ppb by mass, a nickel ion concentration is less than 4,000 ppb by mass, a molybdenum ion concentration is less than 3,000 ppb by mass, and a zinc ion concentration is less than 1,000 ppb by mass.

14. A method for producing acetic acid, comprising, in a distillation column having a nickel base alloy or zirconium as a material and having a plate spacing between a charging mixture feeding plate and a column top vapor withdrawal plate of not less than one plate in terms of actual plates;
feeding crude acetic acid having an iron ion concentration of less than 10,000 ppb by mass, a chromium ion concentration of less than 5,000 ppb by mass, a nickel ion concentration of less than 3,000 ppb by mass, a molybdenum ion concentration of less than 2,000 ppb by mass, a zinc ion concentration of less than 1,000 ppb by mass, a hexyl iodide concentration of less than 510 ppb by mass, and an acetic acid concentration of not less than 80% by mass into the charging mixture feeding plate via a charging pipe having a nickel base alloy or zirconium as a material; and
conducting distillation under such conditions as to give a column bottom temperature of less than 175° C. and as to meet condition (a") as follows and to optionally meet condition (b") as follows:
(a") adjusting a column bottom liquid to an acetate salt concentration of 0.1 ppm by mass to 1% by mass by reducing an added amount of alkali used for neutralization of hydrogen iodide; and
(b") a column bottom liquid has an acetic anhydride concentration of 0.1 ppm by mass to 1% by mass,
to obtain at least:
an overhead stream rich in water; and
purified acetic acid having an iron ion concentration of less than 21,000 ppb by mass, a chromium ion concentration of less than 7,100 ppb by mass, a nickel ion concentration of less than 4,000 ppb by mass, a molybdenum ion concentration of less than 3,000 ppb by mass, and a zinc ion concentration of less than 1,000 ppb by mass.

* * * * *